US012758526B2

(12) United States Patent
Villoslada Diaz

(10) Patent No.: US 12,758,526 B2
(45) Date of Patent: *Oct. 13, 2026

(54) TREATMENT REGIMEN FOR THE TREATMENT OF NEUROLOGICAL DISEASES OR CONDITIONS

(71) Applicant: Accure Therapeutics, S.L., Barcelona (ES)

(72) Inventor: Pablo Villoslada Diaz, Los Altos, CA (US)

(73) Assignee: Accure Therapeutics, S.L., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 19/401,124

(22) Filed: Nov. 25, 2025

(65) Prior Publication Data

US 2026/0076940 A1 Mar. 19, 2026

Related U.S. Application Data

(63) Continuation of application No. 17/773,548, filed as application No. PCT/EP2020/080404 on Oct. 29, 2020, now Pat. No. 12,594,259.

(30) Foreign Application Priority Data

Oct. 30, 2019 (EP) .................................... 19382950

(51) Int. Cl.

*A61K 31/4015* (2006.01)
*A61K 31/18* (2006.01)
*A61K 31/40* (2006.01)
*A61P 27/06* (2006.01)

(52) U.S. Cl.

CPC .......... *A61K 31/4015* (2013.01); *A61K 31/18* (2013.01); *A61K 31/40* (2013.01); *A61P 27/06* (2018.01)

(58) Field of Classification Search

CPC .... A61K 31/4015; A61K 31/18; A61K 31/40; A61P 27/06

See application file for complete search history.

(56) References Cited

U.S. PATENT DOCUMENTS

| | | | |
|---|---|---|---|
| 6,992,064 B2 | 1/2006 | Orts et al. | |
| 8,791,076 B2 | 7/2014 | Villoslada et al. | |
| 9,453,047 B2 | 9/2016 | Villoslada et al. | |
| 10,106,577 B2 | 10/2018 | Villoslada et al. | |
| 12,594,259 B2 | 4/2026 | Villoslada Diaz | |
| 2004/0029811 A1 | 2/2004 | Orts et al. | |
| 2004/0033958 A1 | 2/2004 | Montiel et al. | |
| 2012/0052094 A1* | 3/2012 | Villoslada ............ | C07K 5/0827 514/17.7 |
| 2015/0005239 A1 | 1/2015 | Villoslada et al. | |
| 2017/0121367 A1 | 5/2017 | Villoslada et al. | |

FOREIGN PATENT DOCUMENTS

| | | |
|---|---|---|
| CA | 2427072 A1 | 4/2003 |
| EP | 2289886 A1 | 3/2011 |
| EP | 2611775 B1 | 3/2016 |
| WO | WO-2004/028521 A2 | 4/2004 |
| WO | WO-2012/028959 A1 | 3/2012 |
| WO | WO-2016/081355 A1 | 5/2016 |
| WO | WO-2016/153957 A2 | 9/2016 |
| WO | WO-2018/170319 A1 | 9/2018 |
| WO | WO-2019/099671 A1 | 5/2019 |

OTHER PUBLICATIONS

Malik et al., 82 Neurology 2173-2179 (2014) (Year: 2014).*
Anonymous: "BN201 SAD MAD Study in healthy subjects", Clinicaltrials.gov; XP055685451, 14 pages, Apr. 10, 2019 [retrieved Apr. 14, 2020].
Anonymous: "Neuroprotection Biotech Bionure reports successful Phase 1 Study for Lead Candidate BN201—Bionure", https://bionure.com/neuroprotection -biotech-bionure-reports-successful-phase-1-study-for-lead-candidate-bn201/; [retrieved Apr. 14, 2020]; XP055685481, 2 pages, May 7, 2019.
"Guidance for Industry—Estimating the Maximum Safe Starting Dose in Initial Clinical Trials for Therapeutics in Adult Healthy Volunteers" (FDA, CDER, 30 pages, Jul. 2005.
Guo, et al: "Decreased Neural Stem/Progenitor Cell Proliferation in Mice with Chronic/Nonremitting Experimental Autoimmune Encephalomyelitis", Neurosignals; vol. 18, pp. 1-8, 2010, published online Sep. 29, 2009.
International Search Report and Written Opinion for International Application No. PCT/EP2020/080404, 11 pages, mailed Jan. 20, 2021.
Kezuka, et al: "Analysis of the Pathogenesis of Experimental Autoimmune Optic Neuritis", Journal of Biomedicine and Biotechnology, vol. 2011(294046), pp. 1-5, 2011.

(Continued)

*Primary Examiner* — Timothy R Rozof
(74) *Attorney, Agent, or Firm* — Knowles Intellectual Property Strategies, LLC

(57) ABSTRACT

It relates to BN201 or a pharmaceutically acceptable salt thereof, for use in the treatment of acute optic neuritis that is efficacious for at least 28 days wherein the treatment is administered once a day for 5-7 days.

BN201

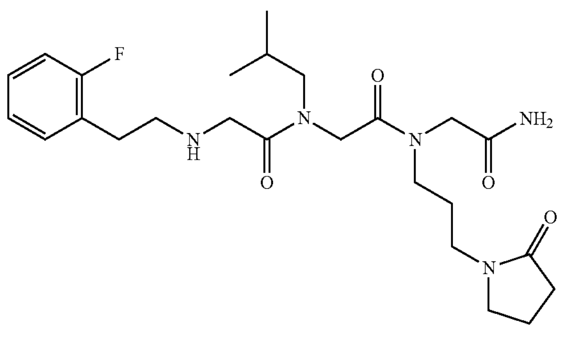

6 Claims, 8 Drawing Sheets

(56) References Cited

OTHER PUBLICATIONS

Kibble, A.: European Committee for Treatment and Research in Multiple Sclerosis (ECTRIMS)—37$^{th}$ Congress; Drugs of the Future; 46(12): 1037-1039, Oct. 13-15, 2021.
Masip I., et al: "Design and synthesis of an optimized positional scanning library of peptoids: identification of novel multidrug resistance reversal agents", 13; 1923-1929, XP027637676, Mar. 15, 2005.
NCT04762017—Phase II Clinical Trial Record History "OCS-05 in Patients With Optic Neuritis (ACUITY)," Clinicaltrials.gov; [retrieved Oct. 21, 2025] First posted Feb. 17, 2021; last update posted Sep. 16, 2025.
Patrikios et al.: "447: Remyeliniation is extensive in the subset of multiple sclerosis patients", Journal of Clinical Neuroscience; vol. 15(3), p. 358, Feb. 7, 2008.
Vermersch: "Sphingosine-1-phosphate Receptor Modulators in Multiple Sclerosis"; European Neurological Review, vol. 13(1); pp. 25-30, 2018.
Villoslada: "Neuroprotective therapies for multiple sclerosis and other demyelinating diseases," Mult Scler and Demyelinating Disorders, 1:1, 2016.
Villoslada et al.: "ACT-01 Eposter Abstracts/Descriptions for European Committee for Treatment and Research in Multiple Sclerosis (ECTRIMS) Conference", Mult Scler J, 27; (2S) 600-604, Oct. 15, 2021.
Villoslada et al.: "Axonal and myelin neuroprotection by the Peptoid BN201 in brain inflammation", Neurotherapeutics; vol. 16(3), pp. 808-827, Feb. 27, 2019.
U.S. Appl. No. 19/438,847, filed Jan. 2, 2026, Sherif et al.
U.S. Appl. No. 19/652,855, filed Apr. 20, 2026, Pablo Villoslada Diaz.
Oculis Announces Positive OCS-05 Phase 2 ACUITY Trial in Acute Optic Neuritis, Met Primary Safety Endpoint and Key Secondary Efficacy Endpoints Opening Development Pathways as a Potential First-in-Class Neuroprotective Therapy, Jan. 6, 2025.
Oculis Announces Agreement with FDA on a Special Protocol Assessment (SPA) for Optic Neuritis Registrational Trial, May 7, 2026.
Villoslada et al., "A Phase 1 randomized study on the safety and pharmacokinetics of OCS-05, a neuroprotective disease modifying treatment for Acute Optic Neuritis and Multiple Sclerosis," Nature.com, 2023.

* cited by examiner

Path (D28)

BN201, 10mpk, IP (D28)

BN201, 25mpk, IP (D28)

TREATMENT REGIMEN FOR THE TREATMENT OF NEUROLOGICAL DISEASES OR CONDITIONS

CROSS-REFERENCE TO RELATED APPLICATIONS

The application is a continuation of U.S. patent application Ser. No. 17/773,548, filed Apr. 29, 2022, which is a 35 U.S.C. § 371 national-phase filing of International Application No. PCT/EP2020/080404 (filed Oct. 29, 2020), which claims the benefit of European Patent Application 19382950.4 (filed on Oct. 30, 2019), these applications are incorporated herein by reference in their entirety.

TECHNICAL FIELD

This invention applies to the area of pharmacy. More specifically, the invention relates to the development of a treatment regimens for the treatment of a neurological disease or condition which results in the destruction or degeneration of neurons, axons or myelin.

BACKGROUND ART

Inflammatory neurological diseases or conditions which result in destruction or degeneration of neurons, axons or myelin may include, but are not limited to, various Central Nervous System (CNS) diseases such as multiple sclerosis (MS), Neuromyelitis optica (NMO), optic neuritis, Balo disease, Schilder's disease, transverse myelitis, acute hemorrhagic leukoencephalitis (i.e., Hurst's disease), and Marburg disease (i.e., acute MS). Neurodegenerative diseases include Alzheimer disease, Parkinson disease, Huntington disease, Fronto-Temporal dementia, Amyotrophic Lateral Sclerosis, heredoataxias, or glaucoma. Optic neuropathies are diseases damaging the optic nerve, including Optic Neuritis, Anterior Ischemic Optic Neuropathy, Leber disease, Dominant Optic atrophy or Glaucoma, and toxic, traumatic, tumor-related optic neuropathies.

MS is a degenerative autoimmune disease of the central nervous system (CNS) in which the immune system attacks and damages axons and the myelin protective sheath surrounding nerve fibers, resulting in significant disability. MS is characterized by demyelination, multifocal inflammation, reactive gliosis, and oligodendrocyte and axonal loss.

NMO (also known as Devic's disease or Devic's syndrome) or NMO spectrum disorders (NMOSD) are autoimmune disorders of the CNS in which immune system cells and antibodies mistakenly attack and destroy astrocytes in the optic nerves, brain and the spinal cord, inducing secondary demyelination and axonal loss. Damage to the optic nerves causes optic neuritis which produces swelling and inflammation that causes pain and loss of vision. Damage to the spinal cord causes weakness or paralysis in the legs or arms, loss of sensation, and problems with bladder and bowel function. Because both diseases have similar symptoms and can cause attacks of optic neuritis and myelitis, NMO can be confused with MS, and until recently, was thought to be a severe variant of MS. However, recent studies suggest that NMO and MS are distinct diseases.

Optic neuritis is a demyelinating inflammation of the optic nerve that can be caused by many different conditions, but often occurs in association with MS and NMO. Inflammation can cause loss of vision or even blindness, often because of the swelling and destruction of the myelin sheath covering the optic nerve. Symptoms of optic neuritis include blurred vision, dimming of colors, pain when the eye is moved, blind spots and loss of contrast sensitivity.

The treatment of MS and other demyelinating diseases (including optic neuritis, myelitis, Neuromyelitis Optica) involves three types of therapies: 1) disease modifying drugs (DMD): intended to stop the pathogenesis of the disease and change the disability accumulation; 2) treatment of relapses: aimed to shorten the relapse duration and decrease residual disability; 3) symptomatic therapy: aimed to ameliorate symptoms due to MS disabilities (e.g. pain, spasticity, bladder symptoms, etc.).

With regard to DMDs for MS, at present all approved therapies are for chronic (long-term) administration requiring different administration protocols depending on the drug or the way of administration: 1) Oral drugs are administered daily (fingolimod, siponimod, ozanimod, dimethyl-fumarate and teriflunomide), except for chemotherapy (mitoxantrone or cladribine) that are administered for few days and then is hold for several years; 2) Subcutaneous drugs are administered daily or every several days (interferon beta, glatiramer acetate); 3) Intravenous drugs are administered every few months (1-6-12) depending of the mechanism of action (MoA) (natalizumab, rituximab, ocrelizumab, alemtuzumab, daclizumab, ofatumumab). All of them are monoclonal antibodies (mabs) that work by depleting immune cell populations or preventing T cell migration. All these drugs are immunomodulatory therapies, and none has a primary neuroprotective activity clearly demonstrated (secondary neuroprotection is the result of stopping inflammation by its immunomodulatory activity which prevents central nervous system (CNS) damage). The reason why some drugs are not administered chronically (chemotherapy and mabs) is because their MoA extend well beyond their exposure (e.g. by decreasing specific immune cell populations that requires months to recover from bone marrow).

With regard to the treatment of relapses: at present there are no drugs approved for treating relapses, but the standard of care (SoC) is the use of either intravenous methylprednisolone or oral prednisone at high doses (1 gr/day for 3-5 days). Corticosteroids treatment exert immunomodulatory activity terminating inflammation, but without having shown neuroprotective effects. For this reason, disability is not modified.

Concerning the symptomatic therapy, there are several drugs being used for improving MS symptoms. Almost all are oral drugs administered chronically (daily) for preventing such symptoms. Some of such drugs (phenytoin, amiloride, aminopyridine, epigallocatechin gallate) have been explored as well as neuroprotectants (in chronic administration), but none has been validated so far as neuroprotectants able to change the course (disability of MS or their relapses).

Therefore, at present there are no neuroprotective drugs approved for MS or that are used as SoC. Current drugs are immunomodulatory (claims about neuroprotection are due to the secondary neuroprotection activity, namely less inflammation means less damage). Pulsatile drugs involve either corticosteroids or chemotherapy and they have extended effects beyond their exposure due to their MoA.

Further, the current therapies are associated with significant side effects, such as adverse immune reactions or severe opportunistic infections.

On the other hand, these diseases or conditions which result in the destruction or degeneration of neurons, axons or myelin generally follow a 'hit and run' model, in which an injury is present for a short period of time (e.g. ischemia, inflammation, trauma), but the damage develops along weeks to month, increasing patient's disability and decreasing quality of life. For this reason, treatments which provide prolonged and sustained efficacy are desired.

WO2012028959 discloses neuroprotective peptoids which show efficacy in vitro and in animal models of preventing neuronal and axonal loss as well as preserving myelin, which is associated with better clinical outcomes in models of e.g. Multiple Sclerosis, Optic Neuritis and Glaucoma. However, this document is silent about the in vivo effects of the compounds over time.

Thus, there is a need in the art for new methods of treating these types of neurological diseases or conditions which have prolonged and sustained efficacy while reducing the side-effects.

SUMMARY OF INVENTION

The inventors have found that when the neuroprotective peptoids disclosed in WO2012028959 are administered for a short period of time (e.g. about 5-7 days) in an Animal Model of Acute Optic Neuritis (AON), which is characterized by increased demyelination, increased axonal loss in the optic nerve, and significant reduction in retinal ganglion cell count in the retina of eye, they show not only efficacy at the short term as expected, but also surprisingly efficacy in the long term (up to one month).

This is illustrated in the examples below (FIG. 6-8). In particular, the results show that a short-term administration of the peptoid BN201 (i.e. ([N-(2-(2'-fluorophenyl)ethyl) glycyl]-[N-(2-methylpropyl)glycyl]-N-[3-(2'-oxopyrrolidinyl)-propyl]glycinamide), either intraperitoneally (IP) or intravenously (IV) in a range of doses from 10 to 70 mg/Kg/day for 6 days is able to protect axons against injury both at the short term (7 days, FIG. 5) and also the long term (up to day 28 post-injury, FIG. 8). Indeed, such efficacy was even increased in later time-points. Additionally, BN201 treatment resulted in significant improvement in retinal ganglion cells, and demyelination score both at the short term (FIGS. 3-4) and long term (FIGS. 6-7) when compared to untreated groups.

These results are of critical importance from the clinical perspective because as mentioned above in these diseases damage develops along weeks to months. Thus, the prolonged and sustained efficacy shown by the neuroprotective peptoids disclosed in WO2012028959 allows a discontinuous treatment regimen comprising a short period of time where the drug is administered followed by a long period of time (which extends far beyond the half-life of the drug (8 h)) where no drug is administered.

The reduced exposition to the drug, compared with being exposed to the same drug for the whole period in which disability is being developed, results in lowering side effects, which leads to an improvement on safety, as well as improving patient compliance of the therapeutic regimen.

Besides, the discontinuous treatment regimen of the invention having a long period of time where no drug is administered before the next drug administration also improves treatment patient compliance therefore leading to increased patient adherence and treatment effectiveness. Often patient will receive the treatment at the time of the acute injury while in the hospital and benefit long after that period, without the need of requiring additional injections or administrations.

Phosphorylation events are very transient (10-30 min) and binding to receptors use to extend for less than one day because receptors are internalized and degraded, in addition to the fact that target binding many times is not permanent and dissociation constants can be quite short.

It has been shown that BN201 activates the serum-glucocorticoid (SGK) pathway, including phosphorylation of several of its targets such as Foxo3 or NDRG1. Such activation triggers the trophic factor pathway which results in changes in gene expression patterns for the next few days. Half-life of BN201 is up to 8 h in humans as found in the phase 1 trial in healthy volunteers. Assuming active transportation to the CNS, lack of drug accumulation and the quick clearance of the drug observed in the same phase 1 trial, it was thought that it was unlikely that BN201 exposure extended beyond one day after the last dose (day 6).

Without being bound to theory the unexpected results suggest that the activation of SGK pathway triggers changes that extend for weeks, changing the phenotype of cells well beyond the specific molecular events triggered by the drug. Such effects are probably mediated by the expression of several genes associated with SGK pathway, which translate to proteins and create such beneficial cell phenotype in neurons, astrocytes, oligodendrocytes and/or microglia.

Therefore, a first aspect of the invention relates to a compound of formula (I), or a pharmaceutically or veterinary acceptable salt thereof, or any stereoisomer or mixtures of stereoisomers, either of the compound of formula (I) or of any of its pharmaceutically or veterinary acceptable salts

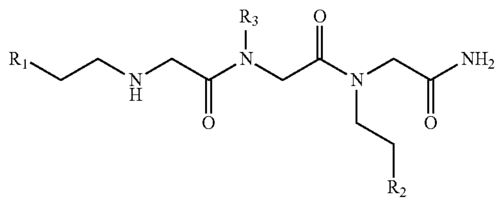

(I)

wherein:

- $R_1$ is phenyl substituted with halogen or trifluoromethyl, and further optionally substituted with one or two substituents selected from the group consisting of halogen, $(C_1\text{-}C_6)$alkyl, $(C_1\text{-}C_6)$alkoxy, and halo$(C_1\text{-}C_6)$alkyl; or alternatively $R_1$ is pyrrolidin-1-yl;
- $R_2$ is 2-oxo-pyrrolidin-1-ylmethyl or sulfamoylphenyl; and
- $R_3$ is selected from the group consisting of propyl, 1-methylethyl, butyl, 2-methylpropyl, pentyl, 1-methylbutyl, 2-methylbutyl, hexyl, 4-methylpentyl, 3-methylpentyl, 2-methylpentyl, and 1-methylpentyl;
- for use in the treatment or prevention of a neurological disease or condition which results in the destruction or degeneration of neurons, axons or myelin, wherein the treatment comprises:
- a) a first time period from 1 to 7 days, wherein the compound is administered once or several times to a subject in need thereof, and
- b) a second time period equal to or longer than 13 days, where in the compound is not administered wherein the second time period takes place after the first time period and before the next administration of the compound.

Therefore, this aspect relates to the use of a compound of formula (I) or a derivative thereof as defined above, for the manufacture of a medicament for the treatment of a neurological disease or condition which results in the destruction or degeneration of neurons, axons or myelin, wherein the treatment comprises:

a) a first time period from 1 to 7 days, wherein the compound is administered once or several times to a subject in need thereof, and b) a second time period equal to or longer than 13 days, where in the compound is not administered, wherein the second time period takes place after the first time period and before the next administration of the compound.

Alternatively, this aspect may also be formulated as a method for the treatment of a neurological disease or condition which results in the destruction or degeneration of neurons, axons or myelin, the method comprising:

a) a first time period from 1 to 7 days, wherein the compound is administered once or several times to a subject in need thereof, including a mammal, particularly a human, and b) a second time period equal to or longer than 13 days, where in the compound is not administered, wherein the second time period takes place after the first time period and before the next administration of the compound.

The compounds of the invention may be formulated in a composition with excipients or carriers. Thus, a second aspect of the invention relates to a pharmaceutical or veterinary composition which comprises a therapeutically effective amount of a compound of formula (I) or a derivative thereof as previously defined, together with one or more pharmaceutically or veterinary acceptable excipients or carriers, for use in the treatment or prevention of a neurological disease or condition which results in the destruction or degeneration of neurons, axons or myelin, wherein the treatment comprises:

a) a first time period from 1 to 7 days, wherein the compound is administered once or several times to a subject in need thereof, and b) a second time period equal to or longer than 13 days, wherein the compound is not administered, wherein the second time period takes place after the first time period and before the next administration of the compound.

DETAILED DESCRIPTION OF THE INVENTION

Figure 1:
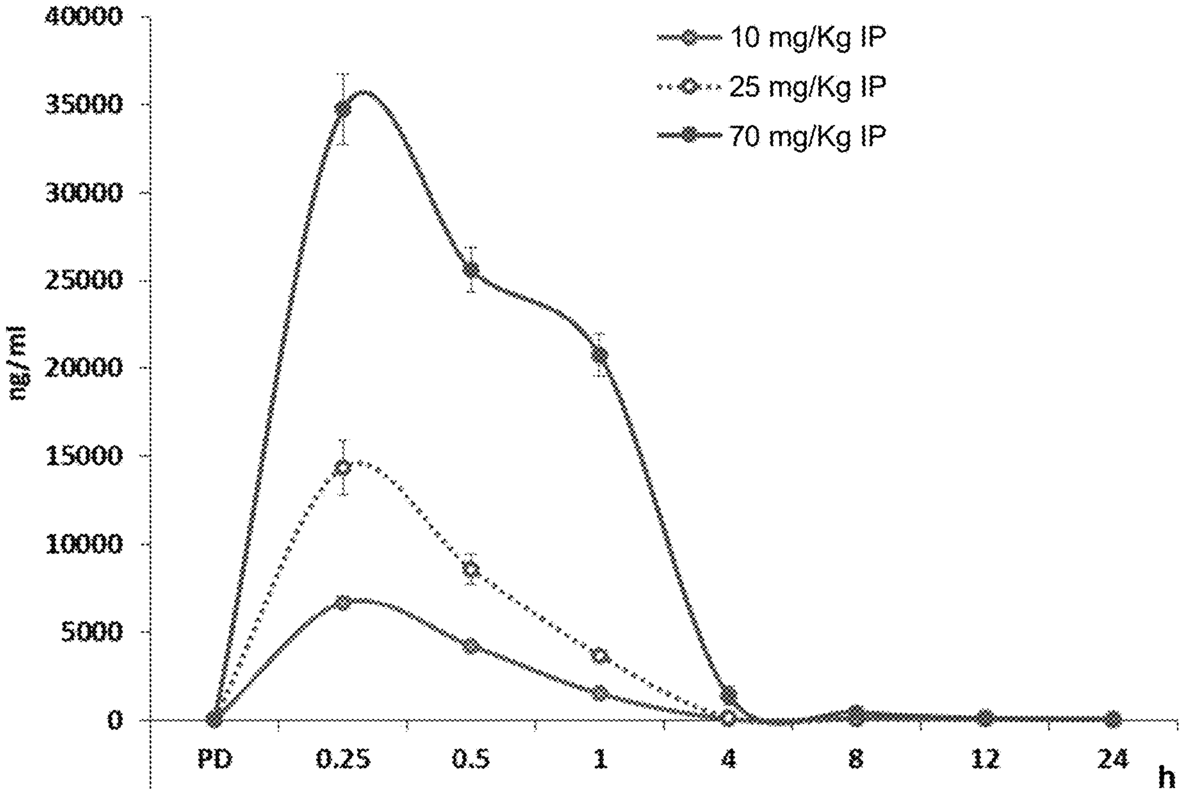
FIG. 1 shows the plasma drug concentration assessed at day 7 after the daily administration of BN201 intraperitoneally (IP) for 6 days in rats at different doses (10, 25 and 70 mg/Kg).

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "about" or "around" as used herein refers to a range of values±10% of a specified value. For example, the expression "about 10" or "around 10" includes ±10% of 10, i.e. from 9 to 11.

Compounds of Formula (I)

As mentioned above, the present invention relates to a new treatment regimen comprising the administration of a compound of formula (I) or derivatives thereof as mentioned herein.

For the purposes of the invention, the term $(C_1-C_n)$alkyl refers to a saturated branched or linear hydrocarbon chain which contains from 1 to n carbon atoms and only single bonds.

Non limiting examples of $(C_1-C_n)$alkyl include methyl, ethyl, 1-propyl, 2-propyl, 1-butyl, 2-methyl-1-propyl, and the like.

The term $(C_1-C_n)$alkoxy refers to a $(C_1-C_n)$alkyl as previously defined which is linked to the rest of a molecule or to another group through an oxygen atom. Non limiting examples of $(C_1-C_n)$alkoxy include methoxy, ethoxy, n-propoxy, isopropoxy, and the like.

The term halo$(C_1-C_n)$alkyl refers to a $(C_1-C_n)$alkyl as previously defined, where some or all of the hydrogen atoms are replaced by fluorine, chlorine, bromine and/or iodine. Non limiting examples of halo$(C_1-C_n)$alkyl include chloromethyl, difluoromethyl, trifluoromethyl, 2-fluoroethyl, 2,2-difluoroethyl, 2,2,2-trifluoroethyl and the like.

A halogen substituent means fluoro, chloro, bromo or iodo.

In one embodiment, optionally in combination with one or more features of the various embodiments described above or below throughout all the description, in the compound of formula (I), $R_1$ is fluorophenyl, more particularly 2-fluorophenyl, 3-fluorophenyl or 4-fluorophenyl, and even more particularly, 2-fluorophenyl.

In another embodiment, optionally in combination with one or more features of the various embodiments described above or below throughout all the description, in the compound of formula (I), $R_1$ is fluorophenyl which is further substituted with one or two substituents selected from the group consisting of halogen, $(C_1-C_6)$alkyl, $(C_1-C_6)$alkoxy, and halo$(C_1-C_6)$alkyl; particularly $R_1$ is fluorophenyl which is further substituted with one or two substituents selected from the group consisting of halogen, $(C_1-C_4)$alkyl, $(C_1-C_4)$ alkoxy, and halo$(C_1-C_4)$alkyl; even more particularly $R_1$ is fluorophenyl which is further substituted with one or two substituents selected from the group consisting of halogen, methyl, ethyl, propyl, isopropyl, methoxy, ethoxy, fluoromethyl, and trifluoromethyl.

In another embodiment, optionally in combination with one or more features of the various embodiments described above or below throughout all the description, in the compound of formula (I), $R_1$ is chlorophenyl, more particularly 2-chlorophenyl, 3-chlorophenyl or 4-chlorophenyl, and even more particularly $R_1$ is 2-chlorophenyl.

In another embodiment, optionally in combination with one or more features of the various embodiments described above or below throughout all the description, in the compound of formula (I), $R_1$ is chlorophenyl which is further substituted with one or two substituents selected from the group consisting of halogen, $(C_1-C_6)$alkyl, $(C_1-C_6)$alkoxy, and halo$(C_1-C_6)$alkyl; particularly $R_1$ is chlorophenyl which is further substituted with one or two substituents selected from the group consisting of halogen, $(C_1-C_4)$alkyl, $(C_1-C_4)$ alkoxy, and halo$(C_1-C_4)$alkyl; even more particularly $R_1$ is chlorophenyl which is further substituted with one or two substituents selected from the group consisting of halogen, methyl, ethyl, propyl, isopropyl, methoxy, ethoxy, fluoromethyl, and trifluoromethyl.

In another embodiment, optionally in combination with one or more features of the various embodiments described above or below throughout all the description, in the compound of formula (I), $R_1$ is bromophenyl, more particularly 2-bromophenyl, 3-bromophenyl or 4-bromophenyl, and even more particularly 2-bromophenyl.

In another embodiment, optionally in combination with one or more features of the various embodiments described above or below throughout all the description, in the compound of formula (I), $R_1$ is bromophenyl which is further substituted with one or two substituents selected from the group consisting of halogen, $(C_1-C_6)$alkyl, $(C_1-C_6)$alkoxy, and halo$(C_1-C_6)$alkyl; particularly $R_1$ is bromophenyl which is further substituted with one or two substituents selected from the group consisting of halogen, $(C_1-C_4)$alkyl, $(C_1-C_4)$ alkoxy, and halo$(C_1-C_4)$alkyl; even more particularly $R_1$ is bromophenyl which is further substituted with one or two substituents selected from the group consisting of halogen, methyl, ethyl, propyl, isopropyl, methoxy, ethoxy, fluoromethyl, and trifluoromethyl.

In another embodiment, optionally in combination with one or more features of the various embodiments described above or below throughout all the description, in the compound of formula (I), $R_1$ is iodophenyl, more particularly 2-iodophenyl, 3-iodophenyl or 4-iodophenyl, and even more particularly 2-iodophenyl.

In another embodiment, optionally in combination with one or more features of the various embodiments described above or below throughout all the description, in the compound of formula (I), $R_1$ is iodophenyl which is further substituted with one or two substituents selected from the group consisting of halogen, $(C_1-C_6)$alkyl, $(C_1-C_6)$alkoxy, and halo$(C_1-C_6)$alkyl; particularly $R_1$ is iodophenyl which is further substituted with one or two substituents selected from the group consisting of halogen, $(C_1-C_4)$alkyl, $(C_1-C_4)$ alkoxy, and halo$(C_1-C_4)$alkyl; more particularly $R_1$ is iodophenyl which is further substituted with one or two substituents selected from the group consisting of halogen, methyl, ethyl, propyl, isopropyl, methoxy, ethoxy, fluoromethyl, and trifluoromethyl.

In another embodiment, optionally in combination with one or more features of the various embodiments described above or below throughout all the description, in the compound of formula (I), $R_1$ is trifluoromethylphenyl, more particularly 2-trifluoromethylphenyl, 3-trifluoromethylphenyl or 4-trifluoromethylphenyl, and even more particularly 2-trifluoromethylphenyl.

In another embodiment, optionally in combination with one or more features of the various embodiments described above or below throughout all the description, in the compound of formula (I), $R_1$ is trifluoromethylphenyl which is further substituted with one or two substituents selected from the group consisting of halogen, $(C_1-C_6)$alkyl, $(C_1-C_6)$ alkoxy, and halo$(C_1-C_6)$alkyl; particularly $R_1$ is trifluoromethylphenyl which is further substituted with one or two substituents selected from the group consisting of halogen, $(C_1-C_4)$alkyl, $(C_1-C_4)$alkoxy, and halo$(C_1-C_4)$alkyl; more particularly $R_1$ is trifluoromethylphenyl which is further substituted with one or two substituents selected from the group consisting of halogen, methyl, ethyl, propyl, isopropyl, methoxy, ethoxy, fluoromethyl, and trifluoromethyl.

In another embodiment, optionally in combination with one or more features of the various embodiments described above or below throughout all the description, in the compound of formula (I), $R_1$ is pyrrolidin-1-yl.

In another embodiment, optionally in combination with one or more features of the various embodiments described above or below throughout all the description, in the compound of formula (I), $R_2$ is 2-oxo-pyrrolidin-1-yl-methyl.

In another embodiment, optionally in combination with one or more features of the various embodiments described above or below throughout all the description, in the compound of formula (I), $R_2$ is sulfamoylphenyl, more particularly 2-sulfamoylphenyl, 3-sulfamoylphenyl, or 4-sulfamoylphenyl, even more particularly 4-sulfamoylethyl.

In another embodiment, optionally in combination with one or more features of the various embodiments described above or below throughout all the description, in the compound of formula (I), $R_3$ is 2-methylpropyl.

In another embodiment, optionally in combination with one or more features of the various embodiments described above or below throughout all the description, in the compound of formula (I), $R_1$ is 2-fluorophenyl or pyrrolidin-1-yl, and $R_2$ is 2-oxo-pyrrolidin-1-ylmethyl or 4-sulfamoylphenyl.

In another embodiment, optionally in combination with one or more features of the various embodiments described above or below throughout all the description, the compound of formula (I) is selected from the group consisting of G79 ([N-(2-(2'-fluorophenyl)ethyl)-glycyl]-[N-(2-methyl-propyl)-glycyl]-N-[3-(2'-oxopyrrolidinyl)-propyl]glycinamide, BN201, Chemical Formula: $C_{25}H_{38}FN_5O_4$; MW 491.5987), G-80 ([N-(2-(2'-fluorophenyl)ethyl)-glycyl]-[N-(2-methyl-propyl)glycyl]-N-[2-(4'-sulfamoyl-phenyl)ethyl] glycinamide, BN119, Chemical Formula: $C_{26}H_{36}FN_5O_5S$; MW 549.658) and G81 ([N-(2-(1-pyrrolidinyl)ethyl)-glycyl]-[N-(2-methyl-propyl)glycyl]-N-[2-(4'-sulfamoyl-phenyl)ethyl]glycinamide, Formula: $C_{24}H_{40}N_6OS$; MW 524.6766):

G79 (BN201)

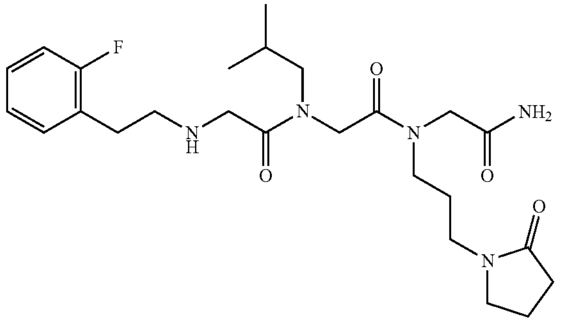

G80 (BN119)

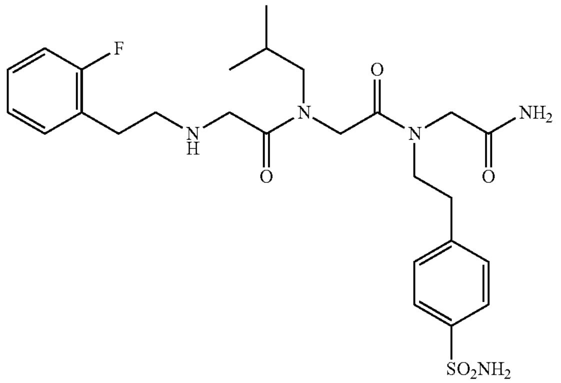

-continued

G81 (BN120)

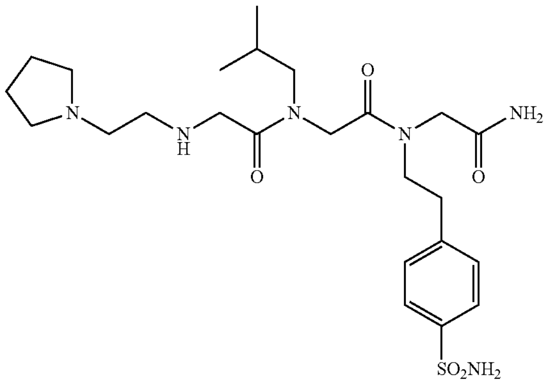

Compounds of formula (I) can be prepared as disclosed in WO2012028959.

There is no limitation on the type of salt of the compounds of formula (I) that can be used, provided that these are pharmaceutically or veterinary acceptable when they are used for therapeutic purposes. The term "pharmaceutically or veterinary acceptable salts", embraces salts commonly used to form alkali metal salts and to form addition salts of free acids or free bases. The preparation of pharmaceutically or veterinary acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of the compounds of formula (I) with a stoichiometric amount of the appropriate pharmaceutically or veterinary acceptable base or acid in water or in an organic solvent or in a mixture of them. The compounds of formula (I) and their respective salts may differ in some physical properties, but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically, cosmetically or veterinary acceptable solvents such as water, ethanol and the like are equivalent to the unsolvated form for the purposes of the invention.

Some compounds of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

In all embodiments of the invention referring to the compounds of formula (I), the pharmaceutically or veterinary acceptable salts thereof and the stereoisomers or mixtures of stereoisomers, either of any of the compounds of formula (I) or of any of their pharmaceutically acceptable salts are always contemplated even if they are not specifically mentioned.

Pharmaceutical and Veterinary Compositions

The compounds of formula (I) may form part of a pharmaceutical or veterinary composition. The pharmaceutical or veterinary compositions used in the present invention comprise a therapeutically effective amount of a compound of formula (I) as previously defined, or a pharmaceutically or veterinary acceptable salt thereof, or any stereoisomer or mixtures of stereoisomers, either of the compound of formula (I) or of its pharmaceutically or veterinary acceptable salt, together with one or more pharmaceutically or veterinary acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration.

The expression "pharmaceutically or veterinary acceptable excipients or carriers" refers to pharmaceutically or veterinary acceptable materials, compositions or vehicles. Each component must be pharmaceutically or veterinary acceptable in the sense of being compatible with the other ingredients of the pharmaceutical or veterinary composition. It must also be suitable for use in contact with the tissue or organ of humans and animals without excessive toxicity, irritation, allergic response, immunogenicity or other problems or complications commensurate with a reasonable benefit/risk ratio.

In one embodiment, optionally in combination with one or more features of the various embodiments described above or below throughout all the description, the pharmaceutical or veterinary composition is a solution of the compound of formula (I) as previously defined in saline (NaCl). More particularly, a 2 mg/mL or a 5 mg/mL solution of the compound of formula (I) as previously defined in saline (NaCl).

Treatment Regimen

As mentioned above, the treatment regimen of the invention comprises administering the compound of formula (I) or a composition containing it as previously defined once or several times to a subject in need thereof for a first period of time from 1 to 7 days, and then stopping administration for a period of time equal to or longer than 13 days.

For the purposes of the invention, the term "several times" refers to more than once.

In one embodiment, optionally in combination with one or more features of the various embodiments described above or below throughout all the description, the term several times means from 2 to 42 times, more particularly, 2, 3, 4, 5, 6, 7, 8, 9, 10, 12, 14, 15, 16, 18, 20, 21, 22, 24, 26, 27, 28, 30, 32, 34, 36, 38, 40 or 42 times.

The expressions "once per day", "once a day", "once daily" are used interchangeably and mean that in one day only one dose of the drug is administered.

The treatment regimen of the invention comprises a first time period (where the drug is administered, i.e. drug administration period), and a second time period (where no drug is administered, i.e. free drug period) before the drug is administered again. Thus, once the second time period, where no drug is administered, has finished, the drug is administered at least once more. In one embodiment, optionally in combination with one or more features of the various embodiments described above or below throughout all the description, the treatment regimen of the invention comprises two or more, more particularly 2, 3, 4, 5, 6, 7, 8, 9, or 10, drug administration periods with the corresponding free drug periods between them.

In another embodiment, optionally in combination with one or more features of the various embodiments described above or below throughout all the description, the treatment regimen of the invention is a cyclic treatment which comprises repeating steps a) and b).

For the purposes of the invention, the term "treatment" of a neurological disease or condition which results in the destruction or degeneration of neurons, axons or myelin the disease or condition refers to reduce, stabilize, or inhibit the progression of disease/condition, when the drug is used in the subject exhibiting or having exhibited symptoms or signs of disease onset. The term treatment also includes those cases where there is a high risk of developing the full-blown disease in patients without clinical history of the disease or condition, such as for example patients suffering from Radiologically Isolated Syndrome (RIS) showing brain lesions in the magnetic resonance imaging (MRI) or patients undergoing planned brain surgery, endarterectomy or other intravascular procedures. For example, treatment may refer to reducing accumulation of disability in a subject in need thereof. In some embodiments, treatment may also refer to providing a neuroprotective effect, immunomodulatory response, or some combination thereof.

The term "prevention" may be interchangeably used with the term "prophylactic treatment" and refers to the prophylactic administration of the compound of formula (I) or a composition thereof to a subject and includes prevention of the onset, recurrence or spread of a disease or disorder, or of one or more symptoms thereof.

In the present invention the terms "patient" and "subject" are used interchangeably.

There is no limitation on the administration schedule of step a) which can be used according to the invention provided that the compound of formula (I), or the composition as previously defined, is administered once or several times for a period of time from 1 to 7 days. Thus, for example the compound of formula (I), or the composition as previously defined, may be administered only once or, alternatively, it may be administered more than once for a period of time from 1 to 7 days following different administration schedules. Non-limiting examples of such administration schedule include every 3 hours (Q3 h), every 4 hours (Q4 h), every 6 hours (Q6 h), every 8 hours (Q8 h), every 12 hours (Q12 h), once per day, twice per day, three times per day, four times per day, every day, every two days, every three days, and the like.

In one embodiment, optionally in combination with one or more features of the various embodiments described above or below throughout all the description, the first period of time of step a) is from 2 to 7 days, from 3 to 7 days, from 4 to 7 days, from 5 to 7 days, or from 6 to 7 days.

In one embodiment, optionally in combination with one or more features of the various embodiments described above or below throughout all the description, in step a) the compound or a composition containing it as previously defined is administered several times for a first period of time of 1, 2, 3, 4, 5, 6, or 7 days, more particularly the period of time is 6 or 7 days.

In another embodiment, optionally in combination with one or more features of the various embodiments described above or below throughout all the description, in step a) the compound of formula (I), or a composition containing it as previously defined, is administered several times. More particularly, the compound is administered every 3 hours (Q3 h), every 4 hours (Q4 h), every 6 hours (Q6 h), every 8 hours (Q8 h), every 12 hours (Q6 h), once per day, twice per day, three times per day, four times per day, every day, every two days, or every three days.

In a more particular embodiment, it is administered every day, more particularly, once daily, every 3 hours (Q3 h), every 4 hours (Q4 h), every 6 hours (Q6 h), every 8 hours (Q8 h), or every 12 hours (Q12 h).

In another more particular embodiment, it is administered every two days, or every three days. Even more particularly, in the administration days, the compound of formula (I) or composition containing it is administered once daily, every 3 hours (Q3 h), every 4 hours (Q4 h), every 6 hours (Q6 h), every 8 hours (Q8 h), or every 12 hours (Q12 h).

In another embodiment, optionally in combination with one or more features of the various embodiments described above or below throughout all the description, the compound of formula (I), or the composition as previously defined, is administered for 6 or 7 days once daily.

As mentioned above, the second period of time of step b) where no compound is administered is equal or longer than 13 days. In one embodiment, optionally in combination with one or more features of the various embodiments described above or below throughout all the description, the second period of time where no compound is administered is from 13 days to one year (12 months).

In another embodiment, optionally in combination with one or more features of the various embodiments described above or below throughout all the description, the second period of time where no compound is administered is from 13 days to 3 months.

In another embodiment, optionally in combination with one or more features of the various embodiments described above or below throughout all the description, the second period of time where no compound is administered is from 13 days to 1 month.

In one embodiment, optionally in combination with one or more features of the various embodiments described above or below throughout all the description, the second period of time where no compound is administered is equal or longer than 13, 14, 15, 16, 18, 20, 21, 22, 23, 24, 25, 26, 27, 28, 29, 30, 32, 34, 37, 41, 44, 48, 51, 55, 58, 62, 69, 76, 83, 84, 85, 86, 87, 88, 89, or 90 days. More particularly, the second time period is of 21 or 22 days.

In another embodiment, optionally in combination with one or more features of the various embodiments described above or below throughout all the description, the second period of time where no compound is administered is from 13 to 20 days, from 13 to 21 days, from 13 to 22 days, from 13 to 23 days, from 13 to 24 days, from 13 to 25 days, from 13 to 26 days, from 13 to 27 days, from 13 to 28 days, from 13 to 29 days, from 13 to 30 days, from 13 to 34 days, from 13 to 41 days, from 13 to 48 days, from 13 to 55 days, or from 13 to 62 days, from 13 to 69 days, from 13 to 76 days, from 13 to 83 days, from 13 to 84 days, from 13 to 85 days, from 13 to 86 days, from 13 to 87 days, from 13 to 88 days, from 13 to 89 days, or from 13 to 90 days.

In another embodiment, optionally in combination with one or more features of the various embodiments described above or below throughout all the description, the second period of time where no compound is administered is from 13 to 358 days, from 13 to 359 days, from 13 to 360 days, from 13 to 361 days, from 13 to 362 days, from 13 to 363 days, from 13 to 364 days, or from 13 to 365 days.

In another embodiment, optionally in combination with one or more features of the various embodiments described above or below throughout all the description, the second period of time where no compound is administered is equal to 2 weeks, 3 weeks, 4 weeks, 5 weeks, 6 weeks, 7, weeks, 8 weeks, 9 weeks, 10 weeks, 12 weeks, 15 weeks, 20 weeks, 24 weeks, 28 weeks, 32 weeks, 36 weeks, 1 month, 2 months, 3 months, 4 months, 5 months, 6 months, 7 months, 8 months, 9 months, 10 months, 11 months, or 12 months.

In one embodiment, optionally in combination with one or more features of the various embodiments described above or below throughout all the description, the first period of time is from 2 to 7 days, from 3 to 7 days, from 4 to 7 days, from 5 to 7 days, from 6 to 7 days, or 7 days, and the second period of time where no compound is administered is equal or longer than 13, 14, 15, 16, 18, 20, 21, 22, 23, 24, 25, 26, 27, 28, 29, 30, 32, 34, 37, 41, 44, 48, 51, 55, 58, 62, 69, 76, 83, 84, 85, 86, 87, 88, 89, or 90 days, more particularly, the second time period is of 21 or 22 days.

In one embodiment, optionally in combination with one or more features of the various embodiments described above or below throughout all the description, the first period of time is from 2 to 7 days, from 3 to 7 days, from 4 to 7 days, from 5 to 7 days, from 6 to 7 days, or 7 days, and the second period of time where no compound is administered is from 13 to 20 days, from 13 to 21 days, from 13 to 22 days, from 13 to 23 days, from 13 to 24 days, from 13 to 25 days, from 13 to 26 days, from 13 to 27 days, from 13 to 28 days.

In one embodiment, optionally in combination with one or more features of the various embodiments described above or below throughout all the description, the first period of time is from 2 to 7 days, from 3 to 7 days, from 4 to 7 days, from 5 to 7 days, from 6 to 7 days, or 7 days, and the second period of time where no compound is administered is equal to 13 days, which means that the compound of formula (I), or the composition thereof as previously defined, is administered every 2 weeks; or alternatively the first period of time is from 2 to 7 days, from 3 to 7 days, from 4 to 7 days, from 5 to 7 days, from 6 to 7 days, or 7 days, and the second period of time where no compound is administered is equal to 20 days, which means that the compound of formula (I). or the composition thereof as previously defined, is administered every 3 weeks; or alternatively the first period of time is from 2 to 7 days, from 3 to 7 days, from 4 to 7 days, from 5 to 7 days, from 6 to 7 days, or 7 days, and the second period of time where no compound is administered is equal to 27 days, which means that the compound of formula (I), or the composition thereof as previously defined, is administered every 4 weeks; or alternatively the first period of time is from 2 to 7 days, from 3 to 7 days, from 4 to 7 days, from 5 to 7 days, from 6 to 7 days, or 7 days, and the second period of time where no compound is administered is equal to 34 days, which means that the compound of formula (I), or the composition thereof as previously defined, is administered every 5 weeks, or alternatively the first period of time is from 2 to 7 days, from 3 to 7 days, from 4 to 7 days, from 5 to 7 days, from 6 to 7 days, or 7 days and the second period of time where no compound is administered is equal to 41 days; which means that the compound of formula (I) or the composition thereof as previously defined is administered every 6 weeks. In a more particular embodiment, the compound or composition is administered every day, more particularly, once daily, every 3 hours (Q3 h), every 4 hours (Q4 h), every 6 hours (Q6 h), every 8 hours (Q8 h), or every 12 hours (Q12 h). In another more particular embodiment, in the first period of time, the compound or composition is administered every two days, or every three days. Even more particularly, in the administration days, it is administered once daily, every 3 hours (Q3 h), every 4 hours (Q4 h), every 6 hours (Q6 h), every 8 hours (Q8 h), or every 12 hours (Q12 h).

In one embodiment, optionally in combination with one or more features of the various embodiments described above or below throughout all the description, the first period of time is from 2 to 7 days, from 3 to 7 days, from 4 to 7 days, from 5 to 7 days, from 6 to 7 days, or 7 days, and the second period of time where no compound is administered is from 27 to 30 days, which means that the compound of formula (I), or the composition thereof as previously defined, is administered once a month; or alternatively the first period of time is from 2 to 7 days, from 3 to 7 days, from 4 to 7 days, from 5 to 7 days, from 6 to 7 days, or 7 days, and the second period of time where no compound is administered is from 89 to 91 days, which means that the compound of formula (I), or the composition thereof as previously defined is administered every 3 months; or alternatively the first period of time is from 2 to 7 days, from 3 to 7 days, from 4 to 7 days, from 5 to 7 days, from 6 to 7 days, or 7 days, and the second period of time where no compound is administered is from 364 to 365 days, which means that the compound of formula (I), or the composition thereof as previously defined, is administered once a year. In a more particular embodiment, the compound or composition is administered every day, more particularly, once daily, every 3 hours (Q3 h), every 4 hours (Q4 h), every 6 hours (Q6 h), every 8 hours (Q8 h), or every 12 hours (Q12 h). In another more particular embodiment, in the first period of time, the compound or composition is administered every two days, or every three days. Even more particularly, in the administration days, it is administered once daily, every 3 hours (Q3 h), every 4 hours (Q4 h), every 6 hours (Q6 h), every 8 hours (Q8 h), or every 12 hours (Q12 h).

In another embodiment, optionally in combination with one or more features of the various embodiments described above or below throughout all the description, the compound of formula (I) or the composition as previously defined are administered intravenously.

In another embodiment, optionally in combination with one or more features of the various embodiments described above or below throughout all the description, the compound of formula (I) or the composition as previously defined are administered intraperitoneally.

The compound of formula (I) may be administered according to the treatment regimen of the invention at a dosage from 0.5 to 200 mg/Kg in mice, that corresponds to a Human equivalent dose (HED) from 0.04 mg/Kg to 16.26 mg/Kg [HED calculation throughout this description based on Guidance for Industry estimating the maximum safe starting dose in initial clinical trials for therapeutics in adult healthy volunteers; FDA, CDER, July 2005].

Thus, in one embodiment, optionally in combination with one or more features of the various embodiments described above or below throughout all the description, the compound of formula (I) or the composition as previously defined is administered only once or alternatively on a daily basis at a dosage in humans that is equivalent to a dosage in mice from 0.5 to 200 mg/Kg, more particularly 2 to 100 mg/Kg, even more particularly from 5 to 75 mg/Kg, and even more particularly from 10 to 70 mg/Kg of the compound of formula (I).

In another embodiment, optionally in combination with one or more features of the various embodiments described above or below throughout all the description, the compound of formula (I) or the composition as previously defined is administered only once or alternatively on a daily basis at a dosage in humans that is equivalent to a dosage in mice selected from the group consisting of about 200 mg/Kg, about 175 mg/Kg, about 150 mg/Kg, about 125 mg/Kg, about 100 mg/Kg, about 75 mg/Kg, about 70 mg/Kg, about 60 mg/Kg, about 55 mg/Kg, about 50 mg/Kg, about 45 mg/Kg, about 40 mg/Kg, about 35 mg/Kg, about 30 mg/Kg, about 25 mg/Kg, about 20 mg/Kg, about 15 mg/Kg, about 10 mg/Kg, about 5 mg/Kg, about 2.5 mg/Kg, about 2 mg/Kg, about 1.5 mg/Kg, about 1.0 mg/Kg, and about 0.5 mg/Kg of the compound of formula (I). More particularly, the compound of formula (I) or the composition as previously defined is administered at a dosage in humans that is equivalent to a dosage in mice selected from the group consisting of about 70 mg/Kg, about 25 mg/Kg, and about 10 mg/Kg of the compound of formula (I).

In the treatment regimen of the invention, the administration of the compound of formula (I) or the composition as previously defined for a short period of time is capable of providing a certain Area Under the Curve ($AUC_{Last}$) and $C_{max}$ values.

The term "Area Under the Curve ($AUC_{Last}$)" refers to the area under the curve from the time of dosing to the last measurable concentration of the compound of formula (I) or the composition as previously defined for the first time period as mentioned above. The maximum measured plasma concentration of the administered drug is referred to as "$C_{max}$".

In one embodiment, optionally in combination with one or more features of the various embodiments described above or below throughout all the description, the administration of the compound of formula (I) or the composition as previously defined for the first time period as mentioned above is capable of providing an Area Under the Curve ($AUC_{Last}$) from 1 to 100,000 h*ng/mL, more particularly 500 to 80,000 h*ng/mL, even more particularly from 6,000 to 66,000 h*ng/mL.

In another embodiment, optionally in combination with one or more features of the various embodiments described above or below throughout all the description, the administration of the compound of formula (I) or the composition as previously defined for the first time period as mentioned above is capable of providing an Area Under the Curve ($AUC_{Last}$) from 6,000 to 9,000 h*ng/mL.

In another embodiment, optionally in combination with one or more features of the various embodiments described above or below throughout all the description, the administration of the compound of formula (I) or the composition as previously defined for the first time period as mentioned above is capable of providing an Area Under the Curve ($AUC_{Last}$) from 12,000 to 16,000 h*ng/mL.

In another embodiment, optionally in combination with one or more features of the various embodiments described above or below throughout all the description, the administration of the compound of formula (I) or the composition as previously defined for the first time period as mentioned above is capable of providing an Area Under the Curve ($AUC_{Last}$) from 60,000 to 66,000 h*ng/mL.

In another embodiment, optionally in combination with one or more features of the various embodiments described above or below throughout all the description, the administration of the compound of formula (I) or the composition as previously defined for the first time period as mentioned above is capable of providing a $C_{max}$ value from 1 to 100000 ng/ml, more particularly from 500 to 80,000 ng/mL, and more particularly from 3,000 to 40,000 ng/mL.

In another embodiment, optionally in combination with one or more features of the various embodiments described above or below throughout all the description, the administration of the compound of formula (I) or the composition as previously defined for the first time period as mentioned above is capable of providing a $C_{max}$ value from 3,000 to 5,000 ng/mL In another embodiment, optionally in combination with one or more features of the various embodiments described above or below throughout all the description, the administration of the compound of formula (I) or the composition as previously defined for the first time period as mentioned above is capable of providing a $C_{max}$ value from 6,000 to 9,000 ng/mL.

In another embodiment, optionally in combination with one or more features of the various embodiments described above or below throughout all the description, the administration of the compound of formula (I) or the composition as previously defined for the first time period as mentioned above is capable of providing a $C_{max}$ value from 12,000 to 16,000 ng/mL.

In another embodiment, optionally in combination with one or more features of the various embodiments described above or below throughout all the description, the administration of the compound of formula (I) or the composition as previously defined for the first time period as mentioned above is capable of providing a $C_{max}$ value from 30,000 to 36,000 ng/mL.

The plasma concentration AUC and $C_{max}$ can be the determined by standard analytical methods well-known in the art, such as for example, automated or manual immunoassay methods, liquid chromatography or liquid chromatography-mass spectrometry.

Neurological Diseases or Conditions

The present invention relates to a new treatment regimen for the treatment of a neurological disease or condition which results in the destruction or degeneration of neurons, axons or myelin such as MS, NMO, transverse myelitis, recurrent optic neuritis or systemic (rheumatologic) diseases affecting the central nervous system. These neurological diseases include inflammatory diseases, non-inflammatory neurological diseases such as optic neuropathies, and neurodegenerative diseases.

Inflammatory diseases of the central nervous system are diseases triggered by the activation of the immune system and characterized by the presence of inflammatory infiltrates or immune molecules damaging the central nervous system. Such damage includes neuronal and axonal loss as well as loss of myelin and oligodendrocytes and their precursors. Non-limiting examples of inflammatory neurological diseases or conditions which result in the destruction or degeneration of neurons, axons or myelin include demyelinating diseases such as multiple sclerosis (MS), neuromyelitis optica (NMO), optic neuritis, Balo disease, Schilder's disease, transverse myelitis, acute hemorrhagic leukoencephalitis, and Marburg disease.

Optic neuropathies are diseases in which the damage is produced specifically in the optic nerve, leading to vision impairment. Non-limiting examples of optic neuropathies include glaucoma, Anterior Ischemic Optic Neuropathy, and Optic Neuritis, genetic optic neuropathies such as Leber disease and Dominant Optic Atrophy, toxic optic neuropathies, traumatic optic neuropathies, and tumor-related optic neuropathies.

Neurodegenerative diseases are characterized by the progressive loss of neurons and axons, with low levels of reactive inflammation. Such loss is produced by different toxic mechanism such as protein deposition and loss of trophic factor support. Examples of neurodegenerative diseases include without limitation Alzheimer disease, Parkinson disease, Huntington disease, Amyotrophic Lateral Sclerosis, Fronto-Temporal dementia, Lewy Body disease, heredoataxias, glaucoma, among others.

In one embodiment, optionally in combination with one or more features of the various embodiments described above or below throughout all the description, the neurological disease or condition which results in the destruction or degeneration of neurons, axons or myelin is selected from the group consisting of demyelinating diseases, optic neuropathies and neurodegenerative diseases. More particularly, it is selected from the group consisting of multiple sclerosis (MS), neuromyelitis optica (NMO), optic neuritis, Balo disease, Schilder's disease, transverse myelitis, acute hemorrhagic leukoencephalitis, Marburg disease, glaucoma, Anterior ischemic optic neuropathy, Leber disease, Dominant Optic Atrophy, toxic optic neuropathies, traumatic optic neuropathies, tumor-related optic neuropathies, Alzheimer disease, Parkinson disease, Huntington disease, Amyotrophic Lateral Sclerosis, Fronto-Temporal dementia, Lewy Body disease, heredoataxias, and a combination thereof. Even more particularly, it is selected from the group consisting of multiple sclerosis (MS), neuromyelitis optica (NMO), optic neuritis, glaucoma, and a combination thereof.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Evaluation of BN201 at Several Doses in Lysolecithin Induced Acute Optic Neuritis Model in Sprague Dawley Rat

1. AIM OF THE STUDY

The study was carried out in two blocks:

The aim of Block1 was to determine the efficacy of BN201 administered intraperitoneally at various doses (10 mg/Kg, 25 mg/Kg, 70 mg/Kg) and intravenously at 25 mg/Kg in Lysolecithin induced optic neuritis in SD Rats (7 days study).

The aim of Block2 was to determine the efficacy of BN201 in long duration model of lysolecithin induced optic neuritis in SD rats (14 and 28 day study)

2. GENERAL PROTOCOL

- Receipt of animals (Male Sprague Dawley Rats, Age: 12-13 weeks, Body weight range at the time of study initiation: 306.8-385.2 g) and acclimatization of animals for a period of at least one week
- Day 0: Administration of Lysolecithin in optic nerve
- Administration of test compound (BN201) daily (Day 0 to day 6=7 doses in total) intra-peritoneally (IP) at various doses (10 mg/Kg, 25 mg/Kg, 70 mg/Kg) and Intravenously (infusion 25 mg/Kg) over 2 h for block1.
- On day 6, Sampling of blood from block1 for plasma at predetermined time points (8-9 time points) for PK and tissue collection (Eye and optic nerve) for histopathological assessment.
- Determination of plasma levels of BN201 by LC-MS/MS
- Determination of Pharmacokinetic Parameters of BN201 by WinNonlin Analysis
- Test compound administration (IP @10 & 25 mg/Kg) once daily (Day 0 to day 6=7 doses in total) for block2; Tissue collection (Eye and optic nerve collection during termination of the study) on day 14, and 28 for histopathological assessment.

3. ANIMAL CONDITIONING

Animals were maintained in a controlled environment with 22±3° C. temperature, 50±20% humidity, a light/dark cycle of 12 hours each and 15-20 fresh air changes per hour. The animals were housed group wise (3 animals per cage) in individual ventilated cages (IVCs) and autoclaved corncob was used as a bedding material. The animals were fed, ad libitum, with certified Irradiated Laboratory Rodent Diet.

4. STUDY EXECUTION PLAN

Animals were divided into different groups according to the following scheme:

| | | Groups | Animals (total) |
|---|---|---|---|
| Block 1 | Day 1 | G1(n = 2), G2(n = 2), G3(n = 8) and G4(n = 8) | 20 |
| | Day 2 | G1(n = 3), G2(n = 3), G5(n = 8) and G6(n = 8) | 22 |
| Block 2 | Day 1 | G1(n = 5), G2(n = 5), G3(n = 5) for day 28 | 15 |
| | Day 2 | G1(n = 5), G2(n = 5), G3(n = 5) for day 14 | 15 |

5. EXPERIMENTAL GROUPS

Block 1:7 day efficacy groups

| Group | Name | n | Treatment | Dose regiment* |
|---|---|---|---|---|
| 1 | Sham control (healthy) | 5 | Saline IP, 2 mL/Kg | 2 mL/Kg normal saline, IP, once daily for 6 days (7 doses: Day 0 to day 6) |
| 2 | Path control (diseased) | 5 | Saline IP, 2 mL/Kg | |
| 3 | Low dose BN201 IP (10 mg/Kg) | 8 | BN201@10 mg/Kg, IP | |
| 4 | Medium dose BN201 IP (25 mg/Kg) | 8 | BN201@25 mg/Kg, IP | |
| 5 | High dose BN201 IP (70 mg/Kg) | 8 | BN201@70 mg/Kg, IP | |
| 6 | BN201 Medium dose IV infusion (25 mg/Kg) | 8 | BN201@25 mg/Kg IV infusion | BN201@25 mg/Kg, IV infusion over 2 h, once daily (7 doses: Day 0 to day 6) with a dose volume of 5 ml/Kg |

-continued

*Dual cannulated (Jugular and Femoral) rats were used for IV infusion groups. Jugular cannulated rats were used in group 2, 3, 4 and 5. Blood collection was performed through jugular cannula.

*IV infusion-2 h delivery using infusion pumps (through femoral vein)

Block 1:7 day efficacy groups

| | Group | Treatment | n | Animal # | Termination day |
|---|---|---|---|---|---|
| Set 1 | 1 | Saline IP, 2 mL/Kg | 5 | 1 to 5 | Day 14 |
| | 2 | BN201@10 mg/Kg, IP | 5 | 6 to 10 | |
| | 3 | BN201@2 5 mg/Kg, IP | 5 | 11 to 15 | |
| Set 2 | 4 | Saline IP, 2 mL/Kg | 5 | 16 to 20 | Day 28 |
| | 5 | BN201@10 mg/Kg, IP | 5 | 21 to 25 | |
| | 6 | BN201@25 mg/Kg, IP | 5 | 26 to 30 | |

*Induction procedure: 0.8 μL of 1% Lysolecithin (with 0.02% Evan's Blue)

6. TEST ITEM PREPARATION

BN201 was dissolved at room temperature in physiologic solution (NaCl 0.9%). The stock solution was prepared at a strength of 100 mg/mL and stored at 20° C. in multiple aliquots. On the day of the experiment the above solution was thawed, and sufficient quantity was withdrawn for further dilution. A working solution of 5 mg/ml for Group 3 to 5 was prepared by diluting the stock solution in normal saline. For IV infusion 2 mg/ml was prepared daily (day 0 to day 6).

7. DISEASE INDUCTION PROCEDURE

Animals were anesthetized; the shaved skin was disinfected with 75% ethanol. A 1 cm incision was made in the skin above the orbit of an eye. The lacrimal glands and extraocular muscles were resected to expose 3 mm of the optic nerve under an operating microscope. The dura and arachnoid matter around the optic nerve were opened longitudinally. A small amount of dye was placed on the dura to show the microinjection site. This is done to identify the focal lesion for the histology. Microinjection was performed with a glass micropipette attached to a Hamilton syringe. The pipette was inserted into the optic nerve as superficially as possible at 2 mm posterior to the globe, and 0.8 μL of 1% lysolecithin (with 0.02% Evan's Blue) was slowly pressure-injected into the nerve over approximately 30 seconds. The sham control rats (animals without disease) were injected with 0.02% Evan's Blue in 0.8 μL saline without lysolecithin. After the injection, the skin incision was sutured, and antibiotic solution were administered to prevent infection.

8. TREATMENT PROCEDURE

- Group 1 and 2 served as sham and pathological control respectively and only saline was administered
- Test compound was delivered once at various doses (as mentioned above) through IP or IV infusion in the respective groups. The first dosage was given 1 hour after Lysolecithin injection and repeated once/day until the end of the experiment On day 6, blood was collected at various time points after administration of test item for drug concentration measurement:

Group 3-5 (IP groups): Pre-dose, 0.25, 0.5, 1, 4, 8 h, 12 h & 24 h (8 time points)

Group 6 (IV Infusion group): Pre-dose, then the following times post infusion: 0 h (end of the infusion), 0.25 h, 0.5 h, 1 h, 4 h, 8 h, 12 h & 24 h (9 time points)·

~200 μL of blood per time point was collected from Jugular vein for all the time points in K2EDTA blood collection tubes and stored at 4° C. until plasma separation within 30 minutes. After plasma separation, all the plasma samples were stored in two aliquots at 80° C. until the completion of all the time points. Further, one aliquot of plasma samples was submitted together to the DMG/KG for drug concentration analysis.

9. OBSERVATION AND READOUTS 9.1 Body Weight

Body weight measurement was performed every morning from day 0 to day 7. All animals were observed regularly for clinical signs.

9.2 Histopathology

Animals were euthanized on Day 7 with $CO_2$ and were perfused transcardially with saline and 4% paraformaldehyde. Optic nerves (from globe to chiasm) and eye were removed and were fixed in 1% paraformaldehyde overnight. Eye from all the animals were collected in Davidson's fixative.

All tissues were processed in an automatic tissue processor and embedded in paraffin. Five-micro meter-thick (5 μm) transverse sections were made at the site of injections (at the place of the dye) using a rotary microtome.

Serial sections of each optic nerve were obtained (4-6 sections). Slides were stained with H&E, LFB and Bielschowsky's silver impregnation Staining (BSS) to assess inflammation, demyelination and axonal pathology in optic nerve. Retinal (Eye) sections were stained with H&E staining and used for retinal ganglion cells (RGCs) count.

10. SCORING CRITERIA

Demyelinated areas were measured (in Luxol-fast blue-stained sections) and observational scoring was performed using the following criteria:

0.5 traces of perivascular or subpial demyelination
1 Marked perivascular or subpial demyelination
2 Confluent perivascular or subpial demyelination
3 Massive confluent demyelination (half of spinal cord)
4 Extensive demyelination An observational scoring scale of 0 to 4 used to assess the severity of axonal loss (in Silver Impregnation stained sections) which is as given below:

0 Normal staining of axon with silver impregnation
0.5 Traces of perivascular or subpial loss of axons
1 Marked perivascular or subpial loss of axons
2 Confluent perivascular or subpial loss of axons
3 Massive confluent axonal loss
4 Extensive axonal loss Scoring criteria used for the assessment of inflammation (in H&E sections):

0 Normal: No infiltration
0.5 Traces of perivascular or subpial infiltration
1 Marked perivascular or subpial infiltration
2 Confluent perivascular or subpial infiltration
3 Massive confluent infiltration
4 Extensive infiltration Representative photographs (10× and 20×) were taken using Leica DFC425C camera attached with Nikon Eclipse 80i microscope.

Retinal ganglion cell (RGC) count was performed in H&E stained sections of eye (6 high power field [40×] per animal) to compare the ganglion cell density between the treatment groups.

11. BIOANALYTICAL PROCEDURES 11.1 Sample Preparation

Study samples were processed by protein precipitation method using cold acetonitrile. In brief, 10 μL of plasma was mixed with 200 μL of acetonitrile containing 100 ng/ml-Verapamil as internal standard. The contents were vortexed to ensure mixing and the precipitated protein was removed by centrifugation at 4000 rpm for 15 minutes at 4° C. The supernatant was collected and submitted for Bioanalysis.

11.2 Analytical Parameters

Chromatographic Conditions

| | |
|---|---|
| Mass Spectra | API-4500 (LC-MS/MS) system with analyst 1.7 |
| HPLC | Nexera X2 LC |
| Column | Synergi Polar, 75*2.0 mm, 4 μ |
| Mode | ESI Positive Mode |
| Method | Gradient |
| Mobile phase | 10 mM Ammonium Acetate in water (A) |
| composition | 0.1% Formic acid in Acetonitrile (B) |
| Flow Rate | 800 μL/min |
| Run time | 2 Min |
| Injection Volume | 2 μL |
| Column Oven | 40° C. |
| Auto sampler Temperature | 8° C. |
| Scan Mode | Positive mode |

Gradient Conditions

| Time (min) | % A | % B |
|---|---|---|
| 0 | 95 | 5 |
| 0.01 | 95 | 5 |
| 0.7 | 5 | 95 |
| 1.2 | 5 | 95 |
| 1.4 | 95 | 5 |
| 2 | 95 | 5 |

12. RESULTS 12.1 Body Weight (Blocks 1 & 2)

There were no significant changes in the body weights of rats between sham control and Path control groups when compared by t test on respective day of study during the in-life phase. Treatment with BN201 did not significantly change the body weight when compared to the pathological control group.

12.2 Pharmacokinetic Parameters (Block 1)

Figure 2:
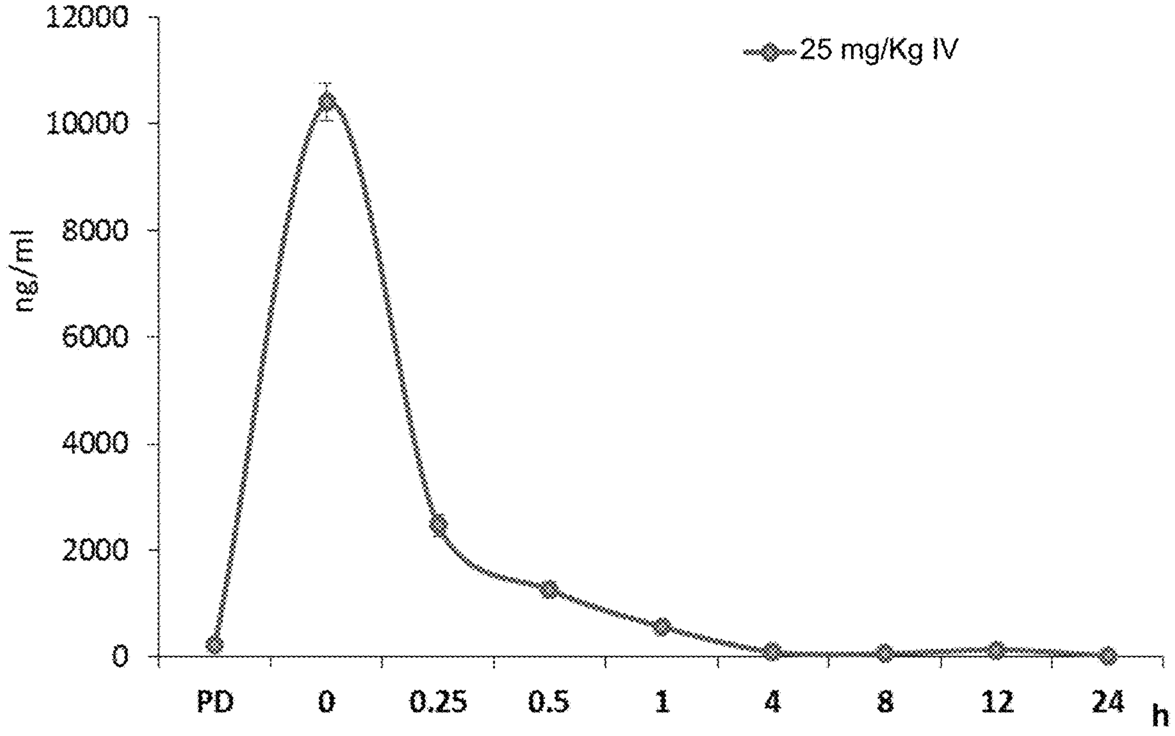
FIG. 2 shows the plasma drug concentration assessed at day 7 after the daily administration of BN201 intravenously (IV) for 6 days in rats at 25 mg/Kg.

Pharmacokinetic parameters for the IP and IV groups are shown in the tables 1 and 2 below and FIGS. 1 and 2.

TABLE 1

| WinNonlin Summary of IP groups (Group 3-5), Total: 7 doses Mean ± SEM PK Parameters | | | |
|---|---|---|---|
| | Dose: mg/Kg | | |
| | 10 | 25 | 70 |
| $C_{max}$ (ng/mL) | 6683.7 ± 348.6 | 14355.5 ± 1539.4 | 34728.4 ± 2011.5 |
| $T_{max}$ (h) | 0.3 ± 0 | 0.3 ± 0 | 0.3 ± 0 |
| AUC $_{(inf)}$ (h*ng/mL) | 6989 ± 381.7 | 14678.4 ± 840.1 | 62761.9 ± 2756.6 |
| $AUC_{last}$ (h*ng/mL) | 6919.6 ± 385.3 | 14549.9 ± 859.2 | 62432.8 ± 2718.5 |
| AUC_% Extrap (obs) | 1 ± 0.2 | 1 ± 0.3 | 0.5 ± 0.1 |
| $t_{1/2}$ (h) | 5.5 ± 0.9 | 5.8 ± 0.2 | 4.7 ± 0.8 |

TABLE 2

| WinNonlin Summary of IV infusion group | |
|---|---|
| PK Parameters | Mean ± SEM |
| $C_{max}$ (ng/mL) | 10396.5 ± 1315.4 |
| $T_{max}$ (h) | 2 ± 0 |
| AUC $_{(inf)}$ (h*ng/mL) | 15358.2 ± 1811 |
| $AUC_{last}$ (h*ng/mL) | 15105.4 ± 1781.7 |
| AUC_% Extrap (obs) | 1.6 ± 0.2 |
| Vd (L/Kg) | 15.8 ± 2.2 |
| CLp (L/h/Kg) | 1.9 ± 0.3 |
| Vdss (L/Kg) | 5.7 ± 1.2 |
| MRT (inf) (h) | 3 ± 0.2 |
| $t_{1/2}$ (h) | 6.2 ± 0.9 |

12.3 Histopathological Assessment 12.3.1 Retinal Ganglion Cell Count (RGC)

Figure 3:
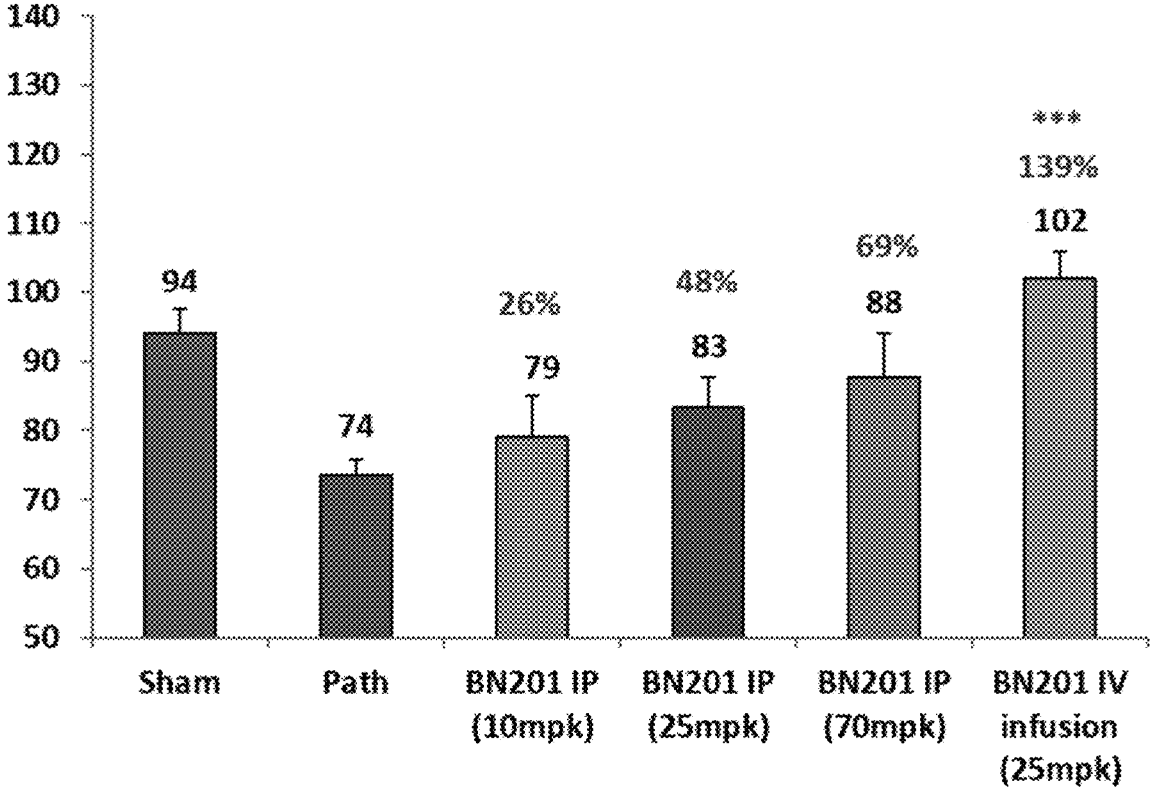
FIG. 3 shows the number of Retinal Ganglion Cells in an Animal Model of Acute Optic Neuritis (AON) assessed at day 7 for sham (healthy), and path (diseased, untreated) control groups and pathological groups treated daily with BN201 intraperitoneally (IP) or intravenously (IV) for 6 days at different doses (mpk=mg/Kg). (*) P value of 0.05; (***) P value of 0.001.
Figure 6:
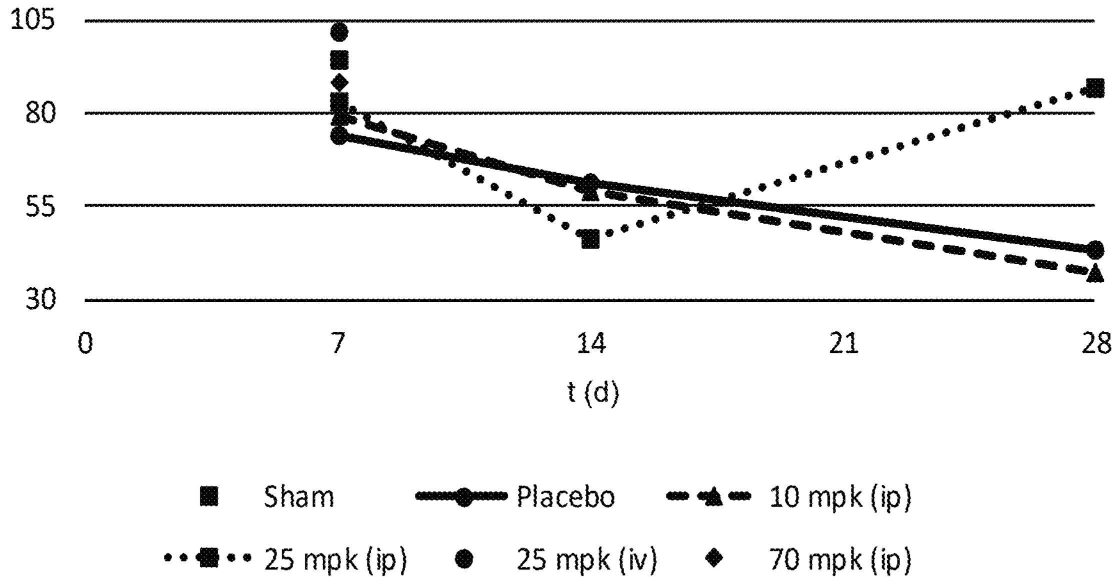
FIG. 6 shows the number of Retinal Ganglion Cells in AON assessed at days 7, 14, and 28 for sham (healthy), and path (diseased, untreated) control groups, and pathological groups treated daily with BN201 intraperitoneally (IP) or intravenously (IV) for 6 days at different doses (mpk=mg/Kg). RGC count was significantly higher in the 25 mpk group by day 28 than placebo ($p<0.05$).

Results of RCG count in Eye for (6 high power field) are shown in FIG. 3 (block 1) and in FIG. 6 (block 2).

RGC (Block1)

Pathological control group showed significantly lower RGC count in 6 random high-power fields (73.6±2.2) compared to (94±3.6) Sham control group. Treatment with BN201 showed a trend of increased RGC count. IV infusion group (25 mg/Kg) showed statistically significant improvement in RGC count compare to pathological control. BN201@25 and 70 mg/Kg IP groups also showed improvement in RGC count with 48% and 69% protection against retinal ganglion cell loss, respectively.

RGC (Block2)

Pathological control group (14 day and 28 day group) showed significantly lower RGC count in 6 random high-power fields. Treatment with BN201 showed improvements on day 28 (25 mg/Kg group).

12.3.2 Demyelination (in Luxol Fast Blue Stained Sections of Optic Nerve)

Figure 4:
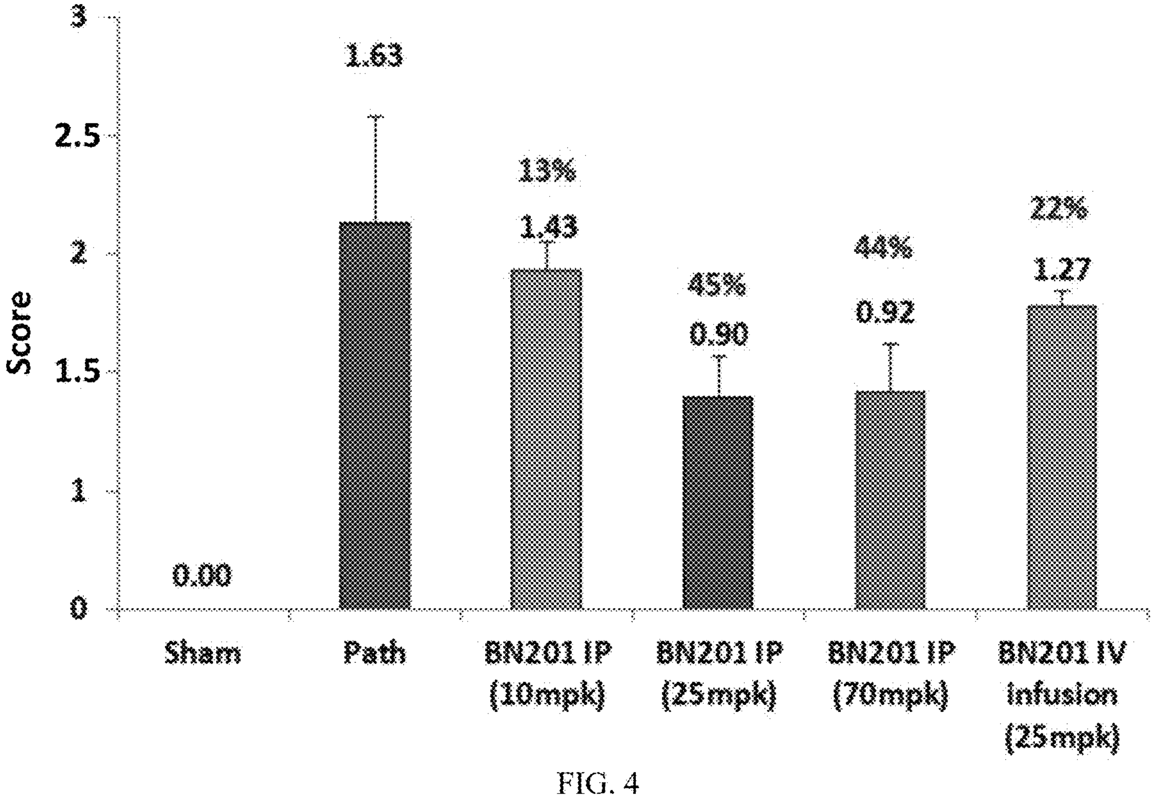
FIG. 4 shows the demyelination score (scale: 0-4) in AON assessed at day 7 for sham (healthy), and path (diseased, untreated) control groups, and pathological groups treated daily with BN201 intraperitoneally (IP) or intravenously (IV) for 6 days at different doses (mpk=mg/Kg).
Figure 7:
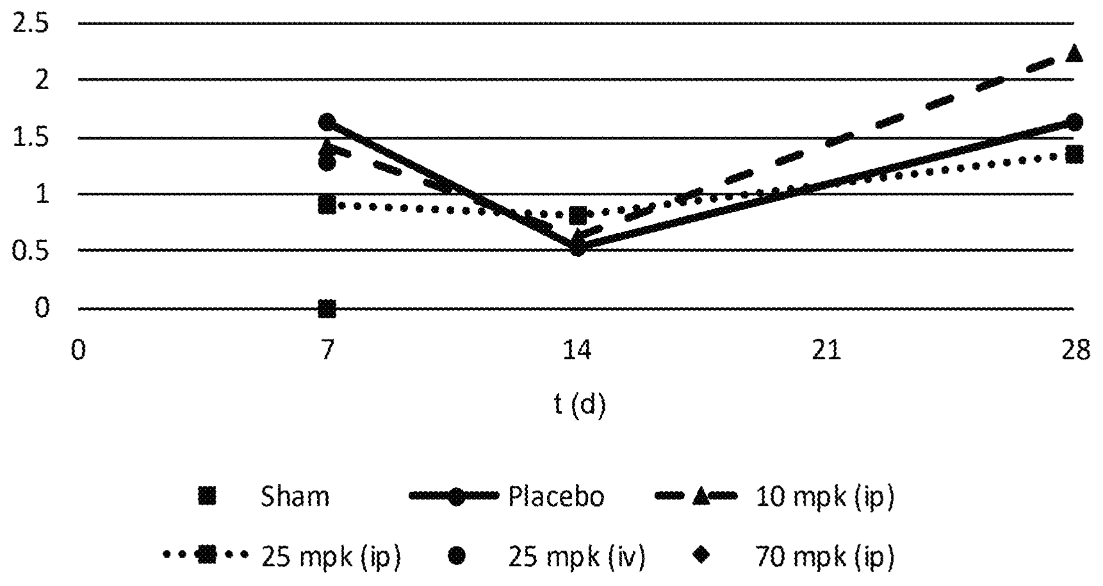
FIG. 7 shows the demyelination score (scale: 0-4) in AON assessed at days 7, 14, and 28 for sham (healthy), and path (diseased, untreated) control groups, and pathological groups treated daily with BN201 intraperitoneally (IP) or intravenously (IV) for 6 days at different doses (mpk=mg/Kg). Demyelination score count was significantly lower in the 10 and 25 mpk group by day 28 than placebo ($p<0.05$).
Figure 9:
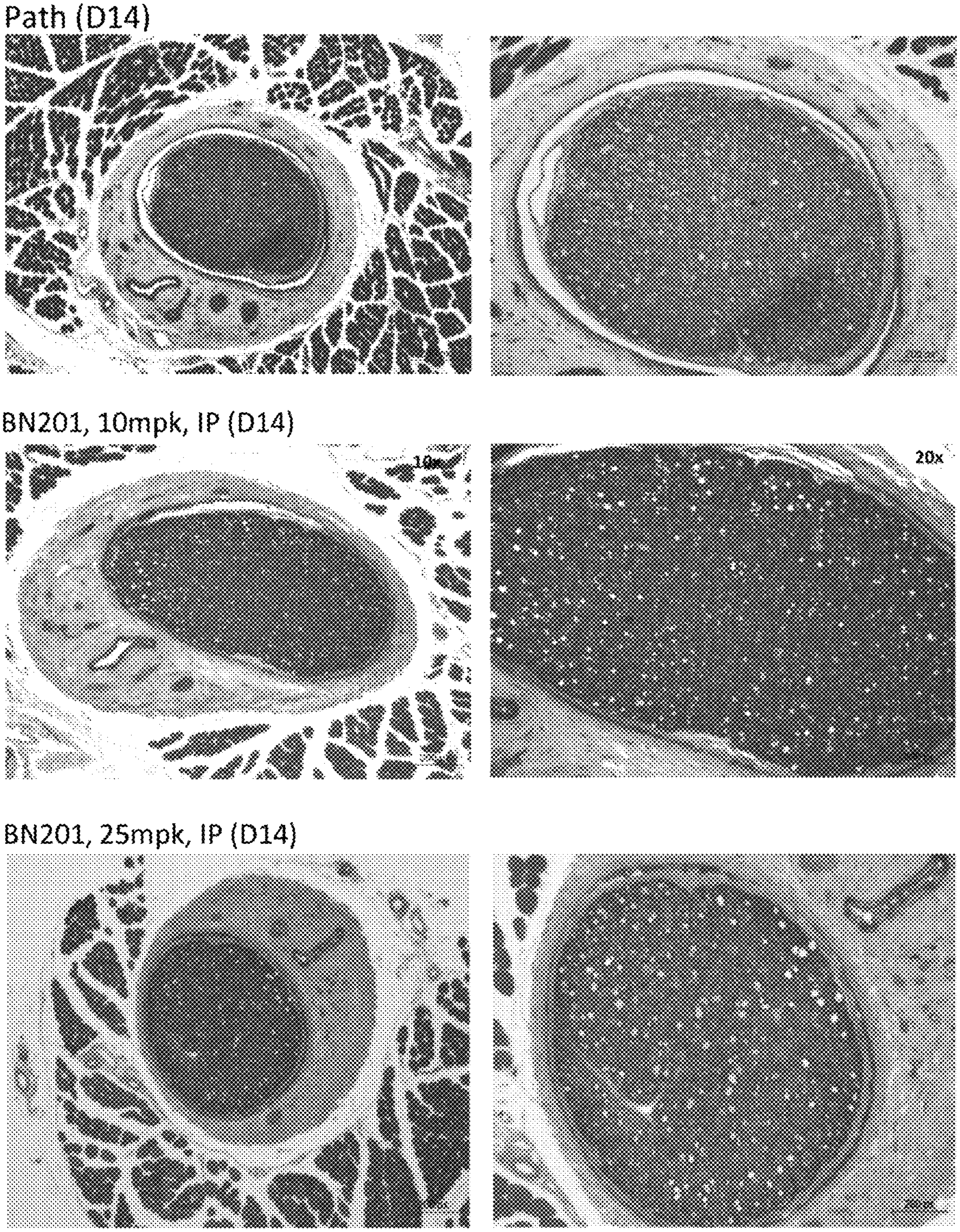
FIG. 9 shows histopathological images of the optic nerve stained with Luxol-fast blue (LFB) in AON assessed at day 14 from the Set 1-path (diseased, untreated) control group, and Set 1 pathological groups treated daily with BN201 intraperitoneally (IP) for 6 days at 10 or 25 mg/Kg to assess demyelination under different magnifications: 10× (left) and 20× (right).
Figure 10:
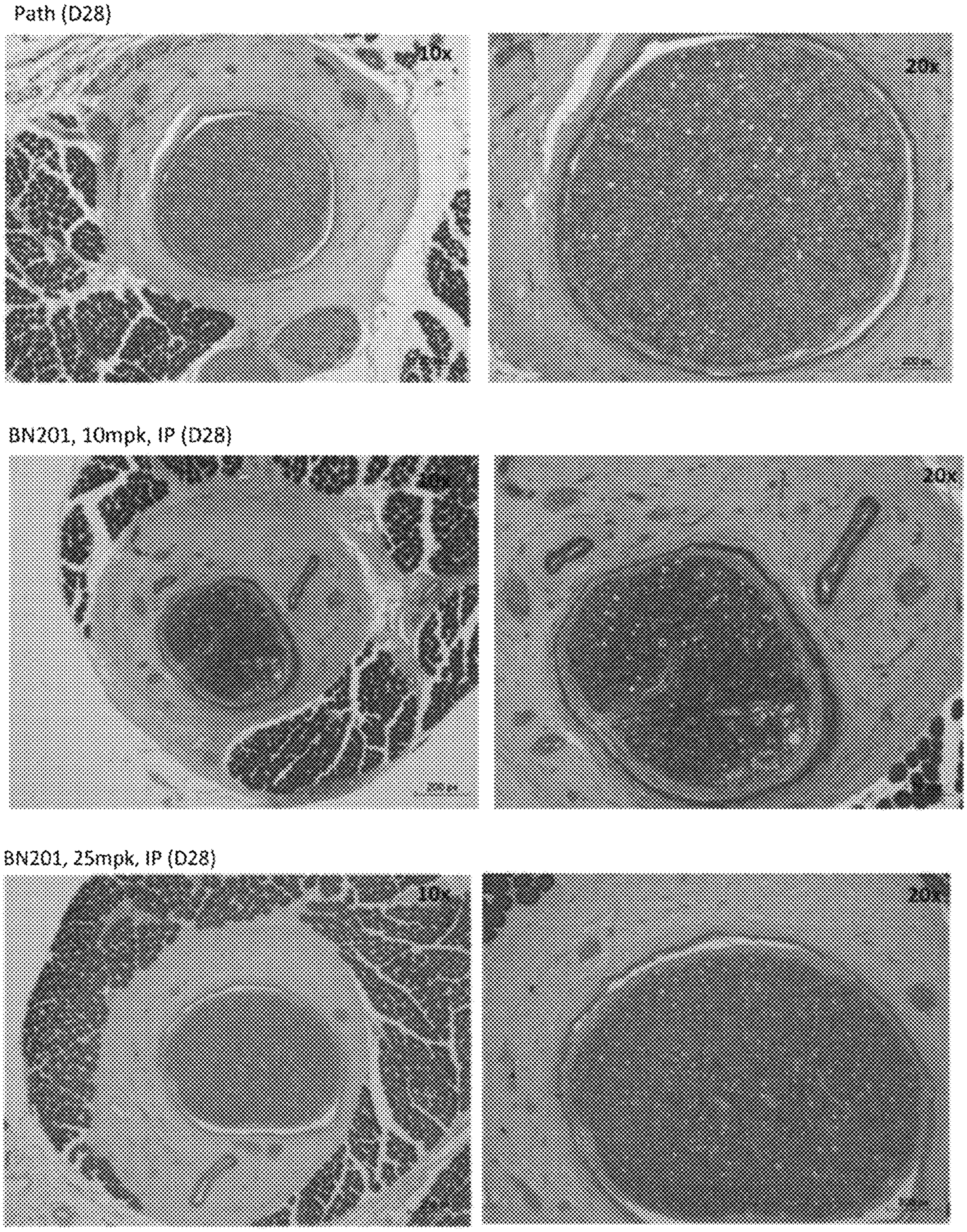
FIG. 10 shows histopathological images of the optic nerve stained with Luxol-fast blue (LFB) in AON assessed at day 28 from the Set 1-path (diseased, untreated) control group, and Set 1 pathological groups treated daily with BN201 intraperitoneally (IP) for 6 days at 10 or 25 mg/Kg to assess demyelination under different magnifications: 10× (left) and 20× (right).

Demyelination score results are shown in FIG. 4 (block 1) and in FIG. 7 (block 2). Histopathological images of the optic nerve stained with LFB assessed at days 14 and 28 to assess demyelination are shown in FIGS. 9 and 10, respectively.

Demyelination (Block1)

Pathological control group showed average demyelination score of 1.6±0.4. Treatment with BN201 @ 10, 25 and 70 mg/Kg IP showed a trend of reduced demyelination score with 13%, 15% and 44% protection, respectively. 25 mg/Kg IV infusion group showed 22% protection against demyelination Demyelination (Block2)

Moderate demyelination was noticed in pathological control groups at 14 and 28 days.

12.3.3 Axonal Loss (in BSS Stained Sections of Optic Nerve)

Figure 5:
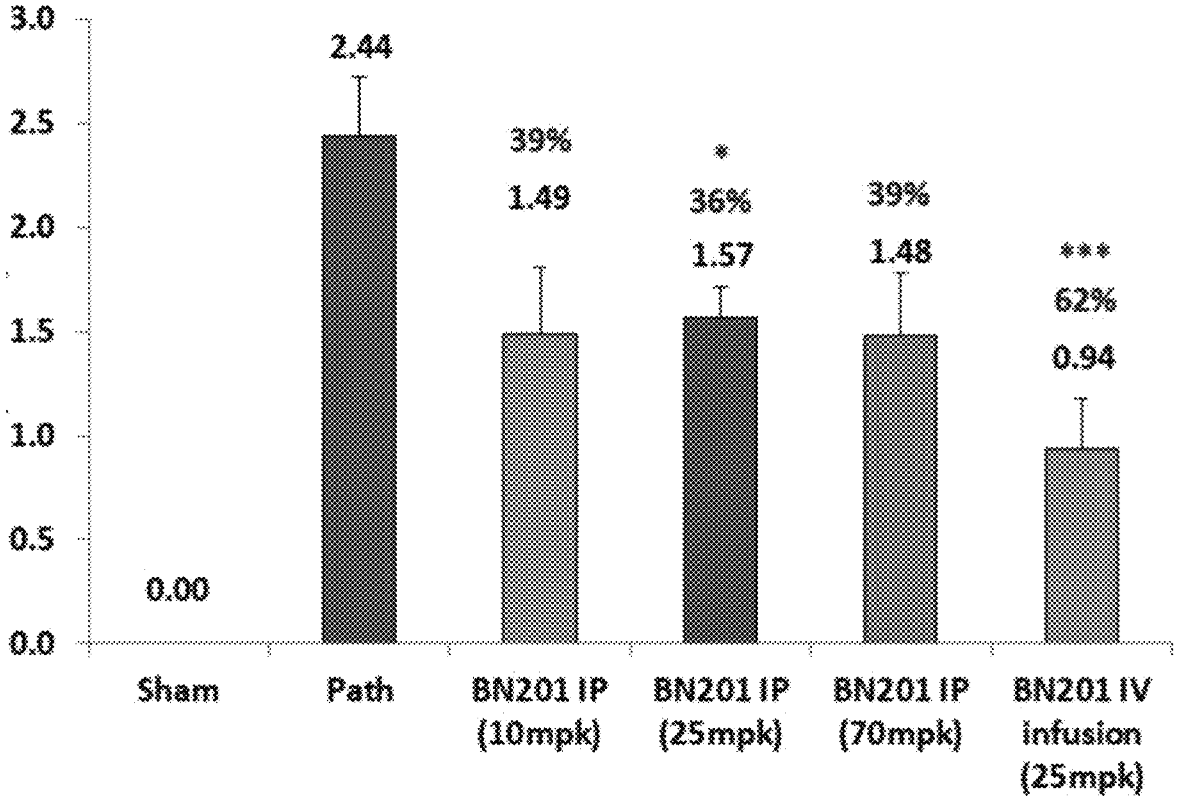
FIG. 5 shows the axonal loss score (scale: 0-4) in AON assessed at day 7 for sham (healthy), and path (diseased, untreated) control groups, and pathological groups treated daily with BN201 intraperitoneally (IP) or intravenously (IV) for 6 days at different doses (mpk=mg/Kg). (*) P value of 0.05. (***) P value of 0.001.
Figure 8:
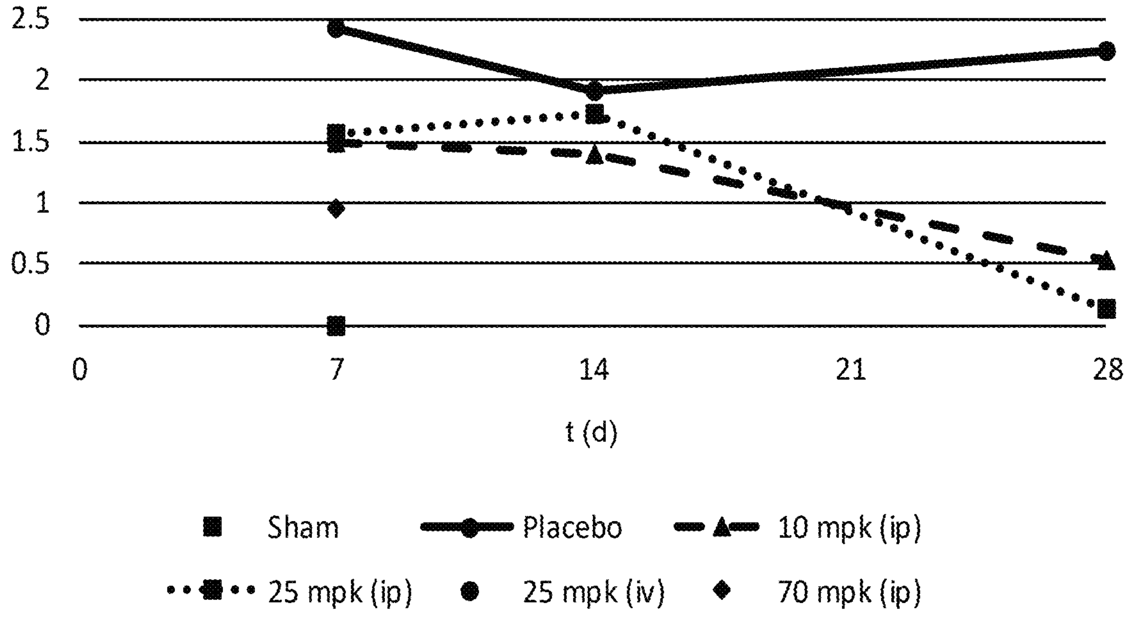
FIG. 8 shows the axonal loss score (scale: 0-4) in AON assessed at days 7, 14, and 28 for sham (healthy), and path (diseased, untreated) control groups, and pathological groups treated daily with BN201 intraperitoneally (IP) or intravenously (IV) for 6 days at different doses (mpk=mg/Kg). Axonal loss score count was significantly lower in the 10 and 25 mpk group by day 28 than placebo ($p<0.05$).
Figure 11:
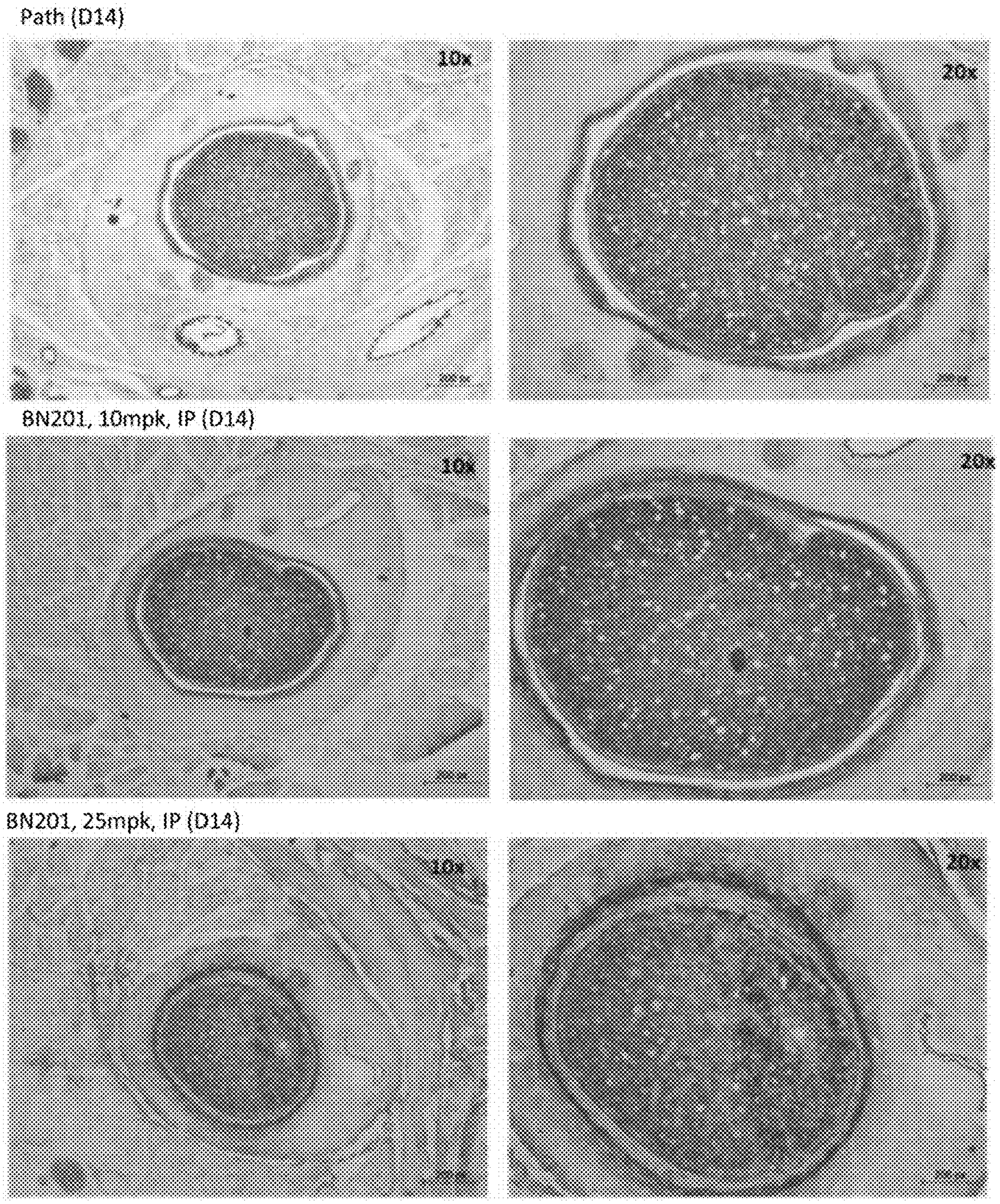
FIG. 11 shows histopathological images of the optic nerve stained with Bielschowsky silver stain (BSS) in AON assessed at day 14 from the Set 1-path (diseased, untreated) control group, and Set 1 pathological groups treated daily with BN201 intraperitoneally (IP) for 6 days at 10 or 25 mg/Kg to assess axonal density under different magnifications: 10× (left) and 20× (right).
Figure 12:
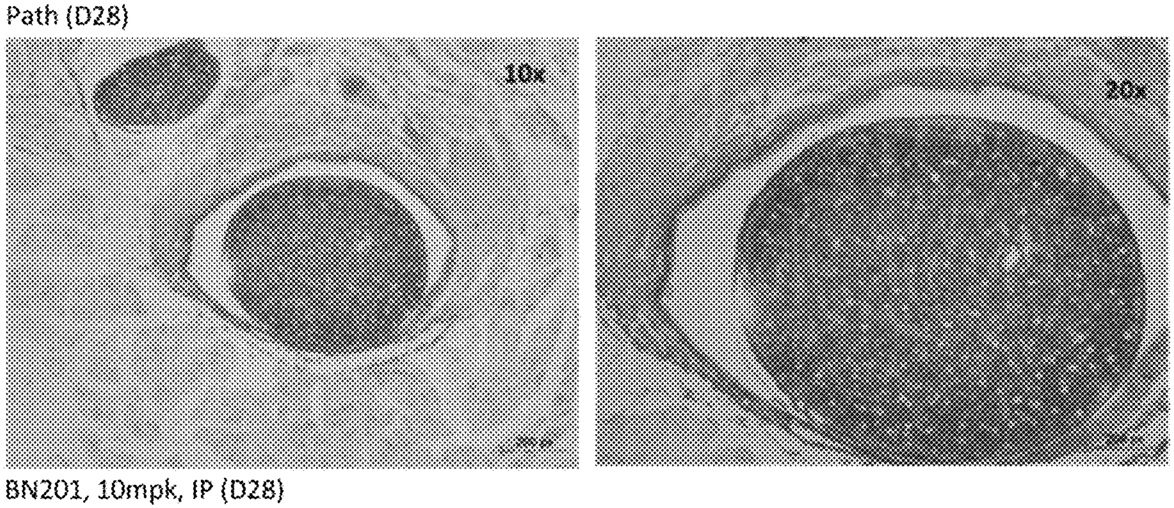
FIG. 12 shows histopathological images of the optic nerve stained with Bielschowsky silver stain (BSS) in AON assessed at day 28 from the Set 1-path (diseased, untreated) control group, and Set 1 pathological groups treated daily with BN201 intraperitoneally (IP) for 6 days at 10 or 25 mg/Kg to assess axonal density under different magnifications: 10× (left) and 20× (right).
Figure 12:
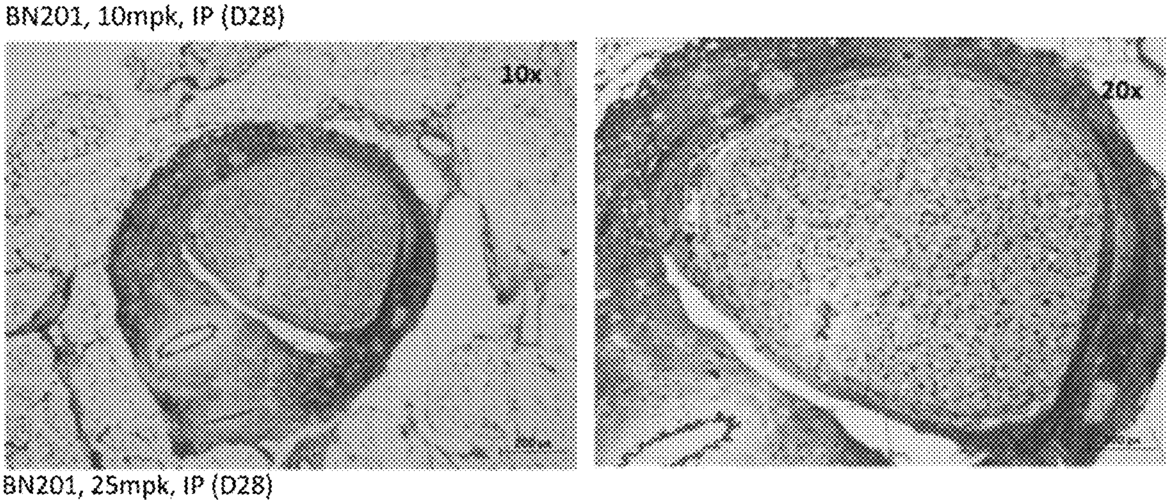
Figure 12:
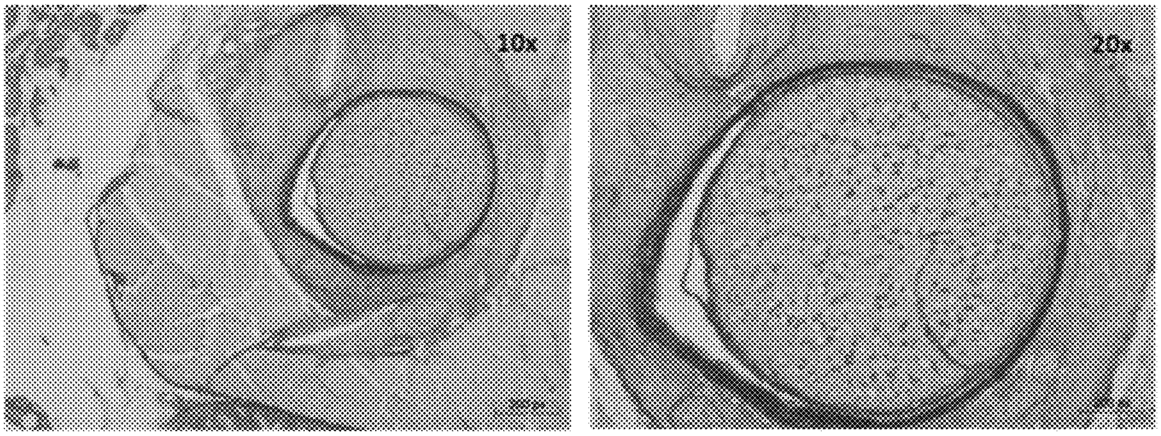

Axonal loss score (Silver impregnation sections, scale: 0-4) is shown in FIG. 5 for block 1 and in FIG. 8 for block 2. Histopathological images of the optic nerve stained with BSS assessed at days 14 and 28 to assess axonal density are shown in FIGS. 11 and 12, respectively.

Axonal Loss (Block1)

Pathological control group showed significant increase in axonal loss score (2.4±0.3) (observed in BSS stained optic nerve sections). Treatment with BN201 @ 10, 25 and 70 mg/Kg IP showed reduced score (36-39% protection). IV infusion resulted in significant protection (62%) against axonal loss.

Axonal Loss (Block2)

Progressive axonal loss was observed on day 14 and day 28 in pathological control groups (score of 1.9 and 2.2 on day 14 and 28 respectively). BN201@10 and 25 mg/Kg showed significant reduction in axonal loss on day 28.

13. CONCLUSIONS

Significant induction of Optic neuritis and retinal ganglion cell loss was observed in pathological control groups (on day 7 (block1), day 14 and 28 (block2)). The optic neuritis was characterized by increased inflammatory cell infiltration (as observed in H&E staining), demyelination (LFB staining) and axonal loss (BSS staining) in the optic nerve and significant reduction in retinal ganglion cell count in the retina of eye in pathological control groups. BN201 treatment resulted in significant improvement in retinal ganglion cells and reduced inflammation, axonal loss and demyelination. Daily IV administration of BN201@25 mg/Kg (2 h infusion) resulted in superior protection against optic neuritis, when compared to BN201@10, 25 and 70 mg/Kg, IP administration.

CITATION LIST

WO2012028959

Guidance for Industry-Estimating the Maximum Safe Starting Dose in Initial Clinical Trials for Therapeutics in Adult Healthy Volunteers (FDA, CDER, July 2005).

I claim:

1. A method for the treatment of acute optic neuritis that is efficacious for at least 28 days, comprising administering an effective amount of a compound of the structure:

BN201

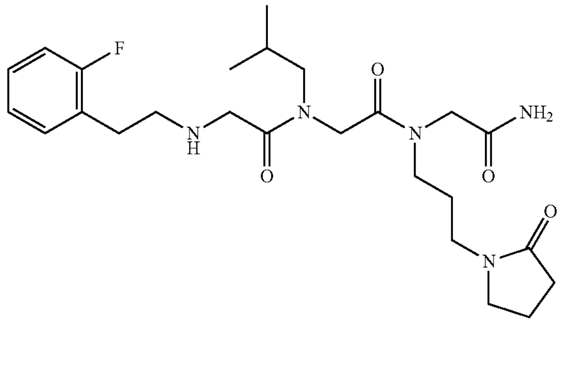

or a pharmaceutically acceptable salt thereof in a pharmaceutically acceptable composition to a human in need thereof;

wherein the treatment is administered once a day for 5-7 days.

2. The method of claim 1, wherein the treatment is administered for 5 days.

3. The method of claim 1, wherein the treatment is administered for 6 days.

4. The method of claim 1, wherein the treatment is administered for 7 days.

5. The method of claim 1, wherein the compound is administered intravenously.

6. The method of claim 1, wherein the compound is administered intraperitoneally.

* * * * *